(12) United States Patent
Kim

(10) Patent No.: US 7,960,345 B2
(45) Date of Patent: Jun. 14, 2011

(54) ANGIOGENESIS INHIBITOR COMPRISING METEORIN AS AN ACTIVE INGREDIENT

(75) Inventor: Kyu-Won Kim, Seoul (KR)

(73) Assignee: Snu R&DB Foundation, Seoul (KR)

( * ) Notice: Subject to any disclaimer, the term of this patent is extended or adjusted under 35 U.S.C. 154(b) by 0 days.

(21) Appl. No.: 12/376,058

(22) PCT Filed: May 2, 2007

(86) PCT No.: PCT/KR2007/002146
§ 371 (c)(1),
(2), (4) Date: Feb. 2, 2009

(87) PCT Pub. No.: WO2008/136541
PCT Pub. Date: Nov. 13, 2008

(65) Prior Publication Data
US 2010/0048471 A1    Feb. 25, 2010

(51) Int. Cl.
*C07K 14/515* (2006.01)
(52) U.S. Cl. .......................... 514/13.3; 514/1.1; 514/7.6
(58) Field of Classification Search .................. None
See application file for complete search history.

(56) References Cited

U.S. PATENT DOCUMENTS

| | | | |
|---|---|---|---|
| 5,192,744 | A | 3/1993 | Bouck et al. |
| 5,200,397 | A | 4/1993 | Deutch et al. |

OTHER PUBLICATIONS

Nishino, J et al. "Meteorin: a secreted protein that regulates glial cell differentiation and promotes axonal extension"; *The EMBO J.* 23(9)1998-2008 (2004).

Park, Ja et al.1 "Isolation of a Hypoxia/Reoxygenation Regulatory Factor in Rat Astrocytes"; *Yakhak Hoeji* 50(2)124-128 (2006) (abstract).

*Primary Examiner* — John D Ulm
(74) *Attorney, Agent, or Firm* — Greenlee Sullivan PC

(57) ABSTRACT

The present invention relates to an angiogenesis inhibitor comprising meteorin as an active ingredient that is highly expressed in astrocytes of the brain and retina in the late embryonic stage and after the birth of a mouse. It is in particular highly detected in astrocyte endfeet surrounding blood vessels and promotes the expression of thrombospondin-1/-2 (TSP-1/-2) via autocrine pathway and thus inhibits angiogenesis. The meteorin of the present invention can be effectively used for pharmaceutical compositions and health foods that prevent vascular diseases by inhibiting angiogenesis.

5 Claims, 18 Drawing Sheets

[Fig. 1]
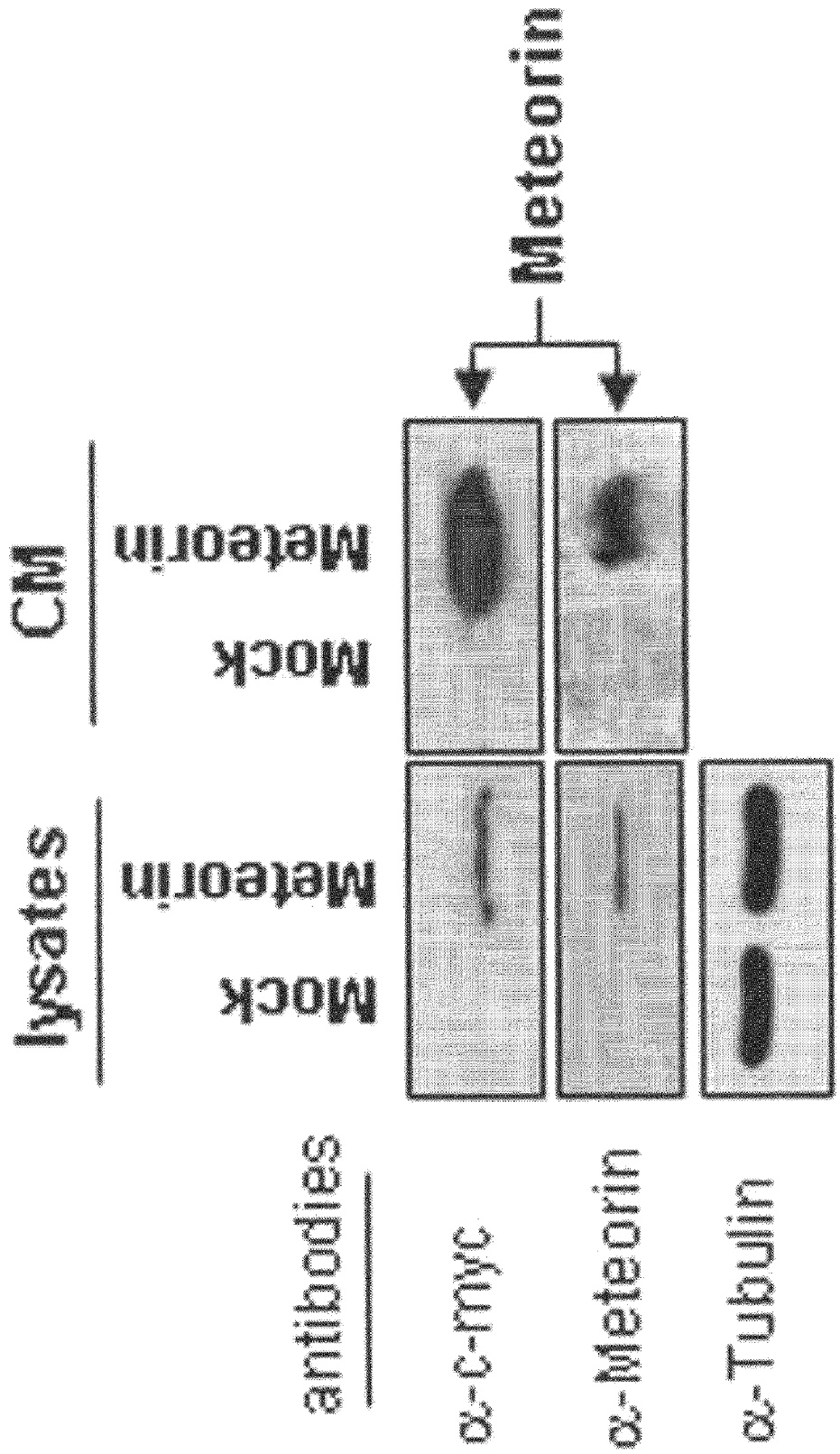

[Fig. 2]
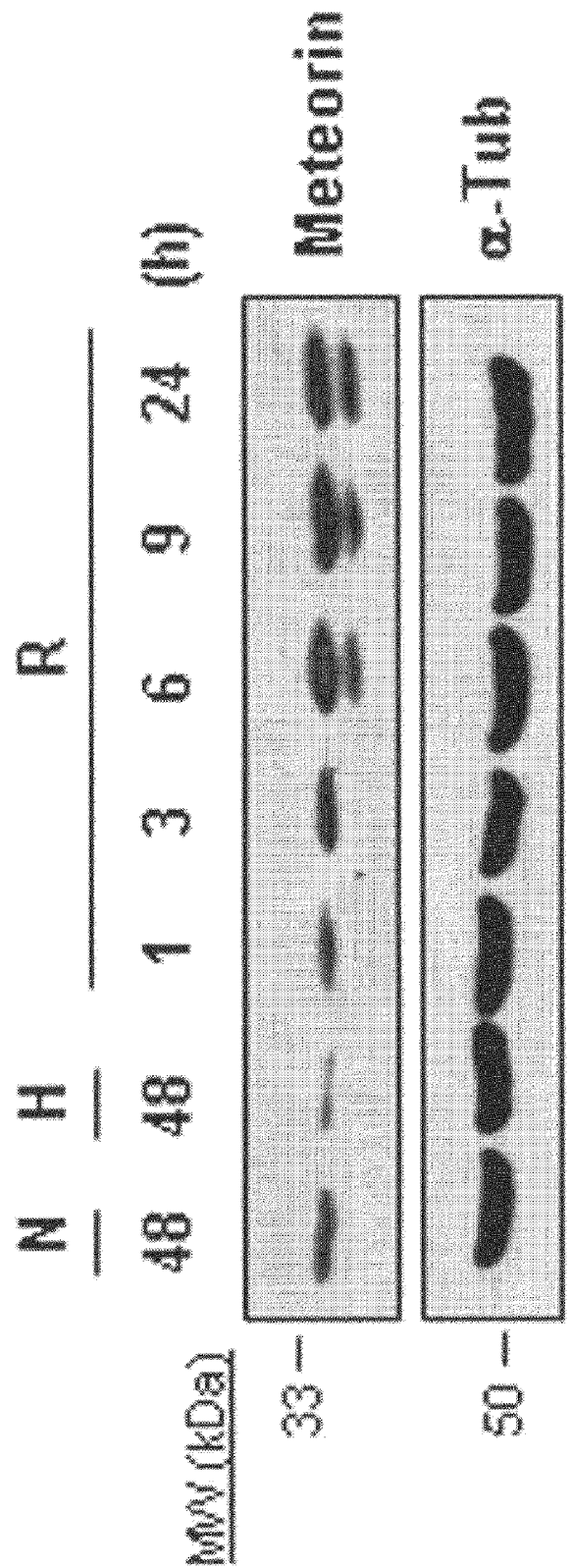

[Fig. 3]
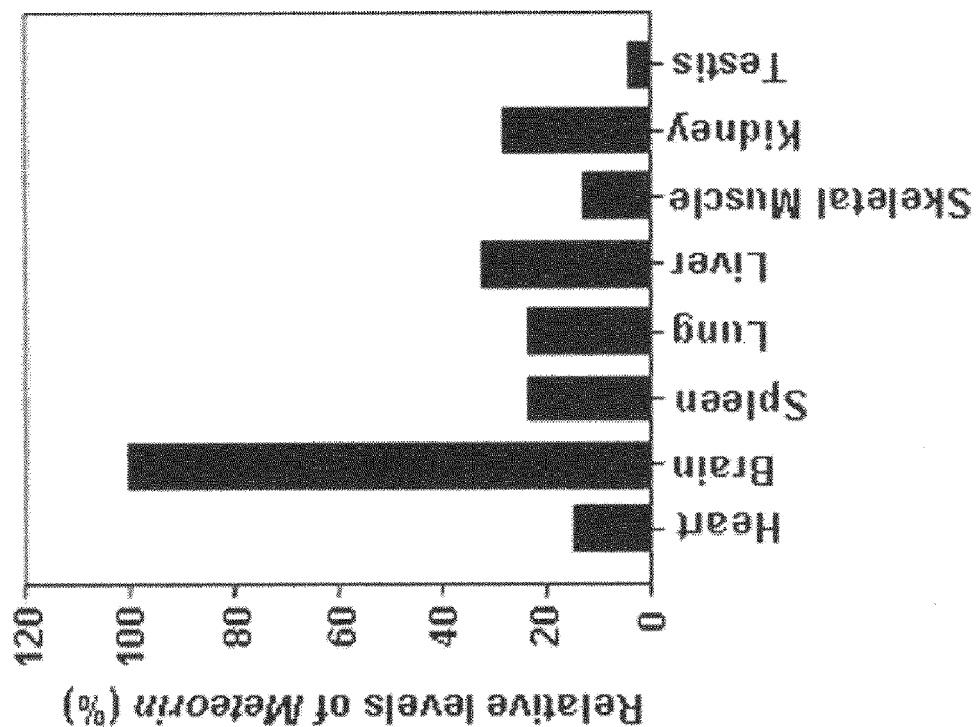
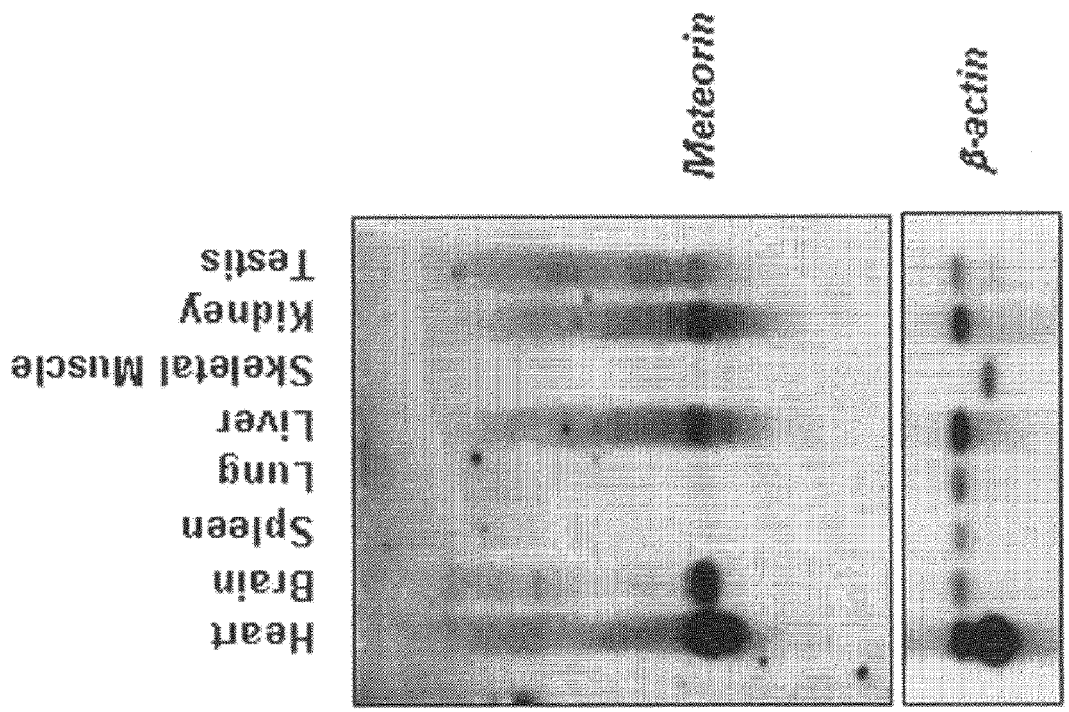

[Fig. 4]
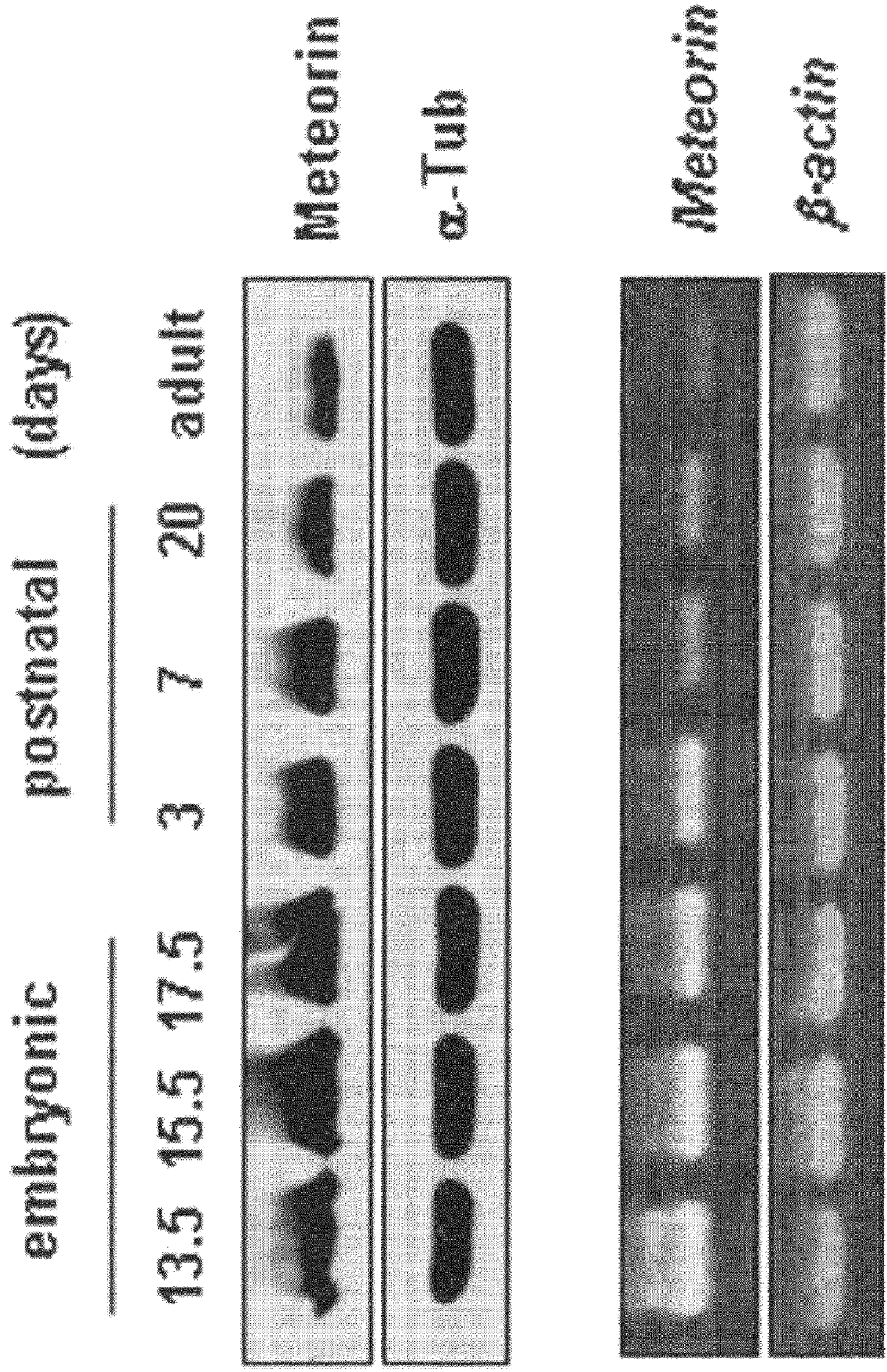

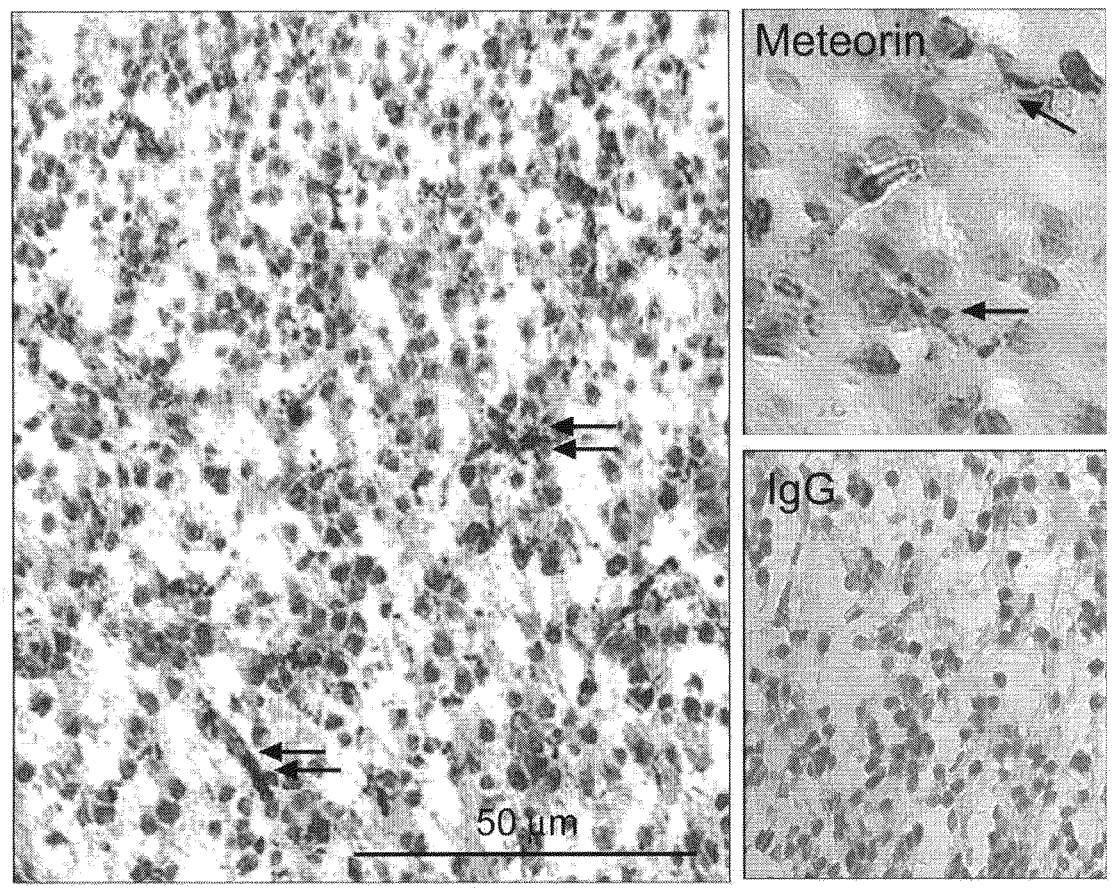
[Fig. 5]

[Fig. 6]
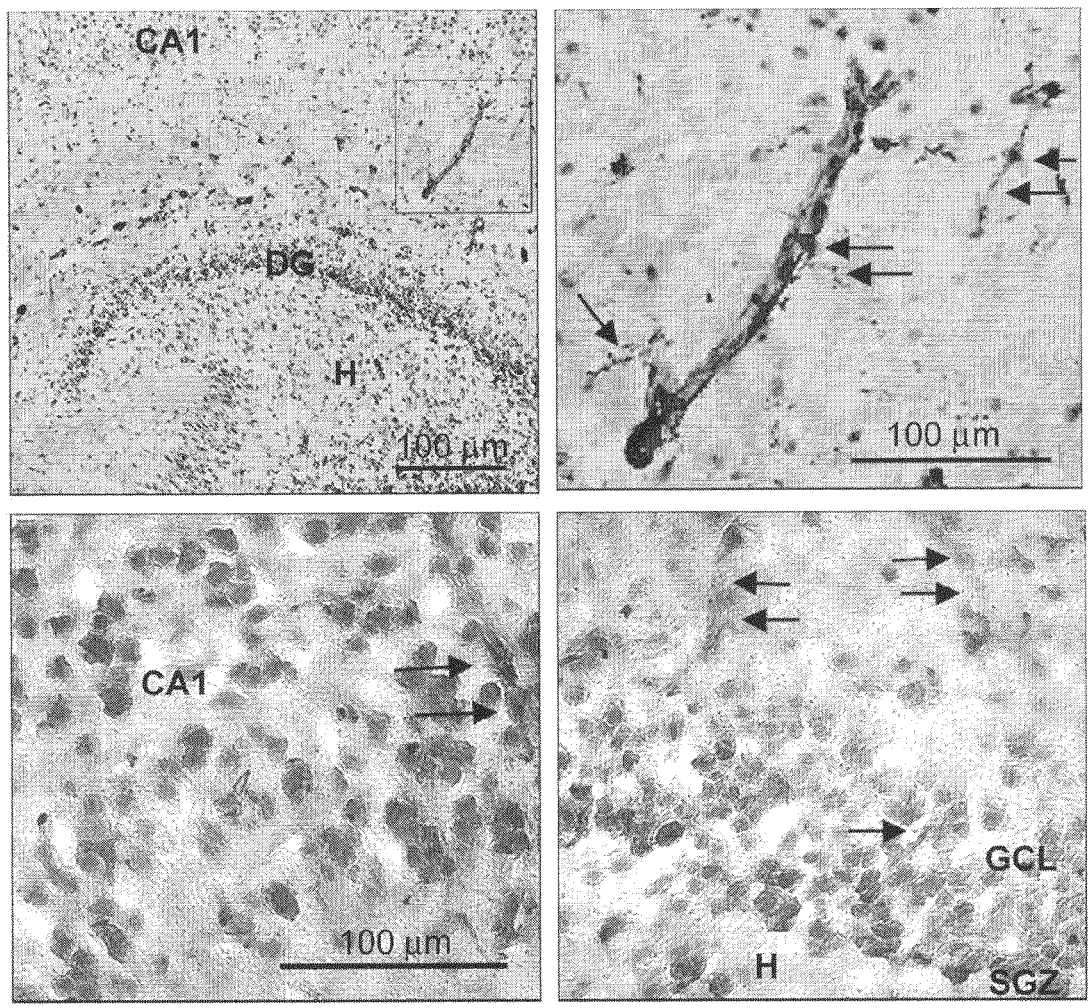

[Fig. 7]
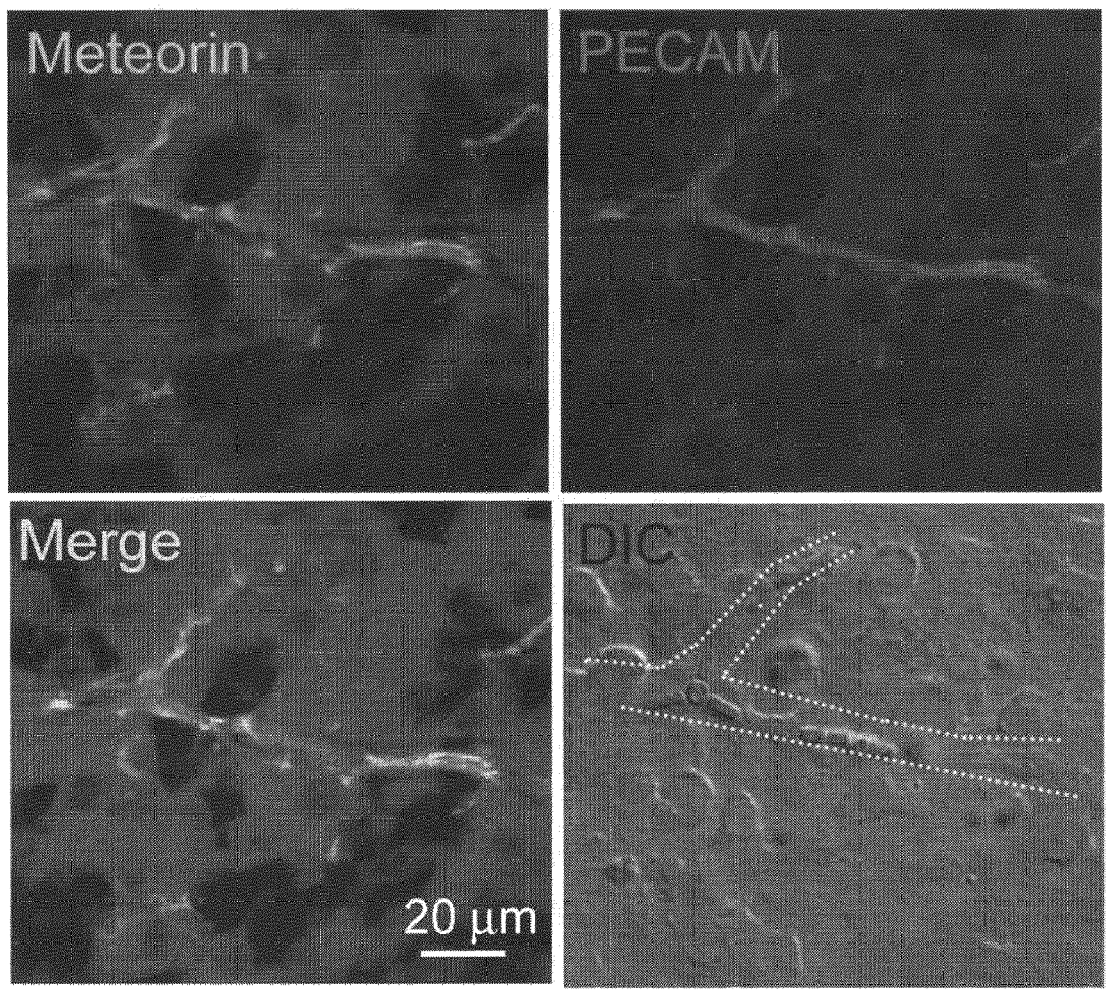

[Fig. 8]
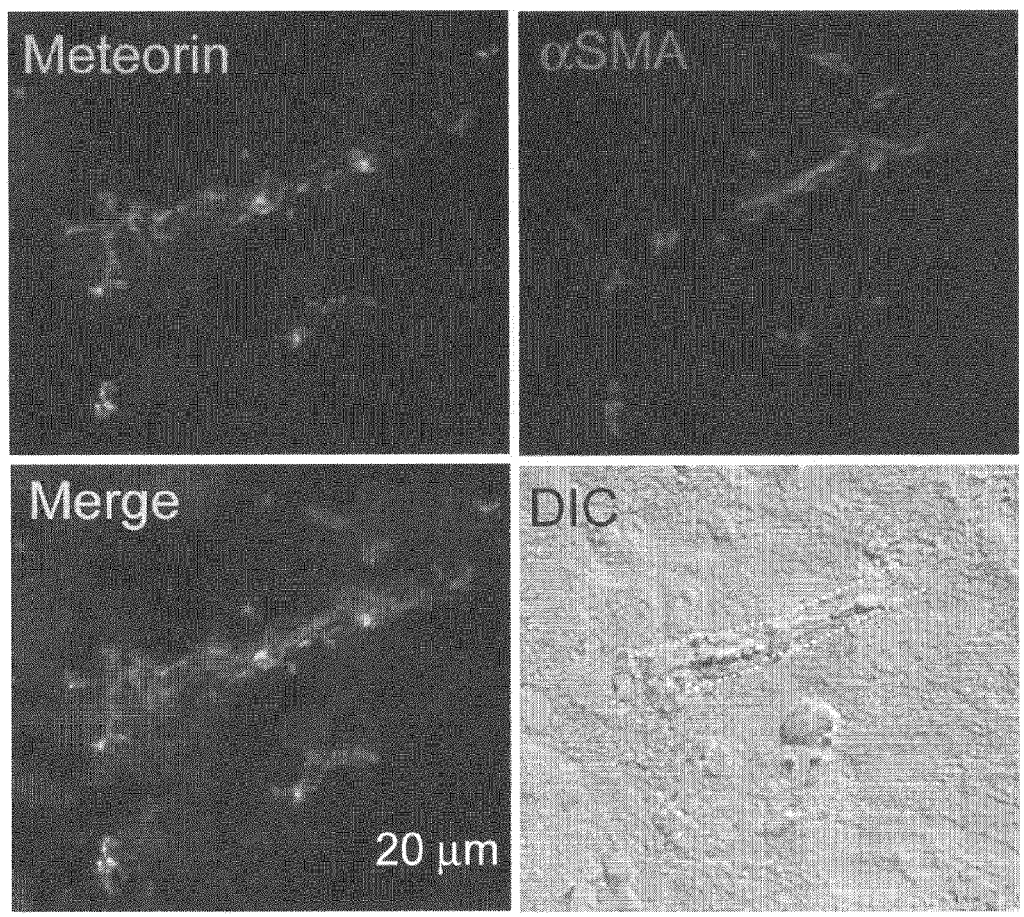

[Fig. 9]
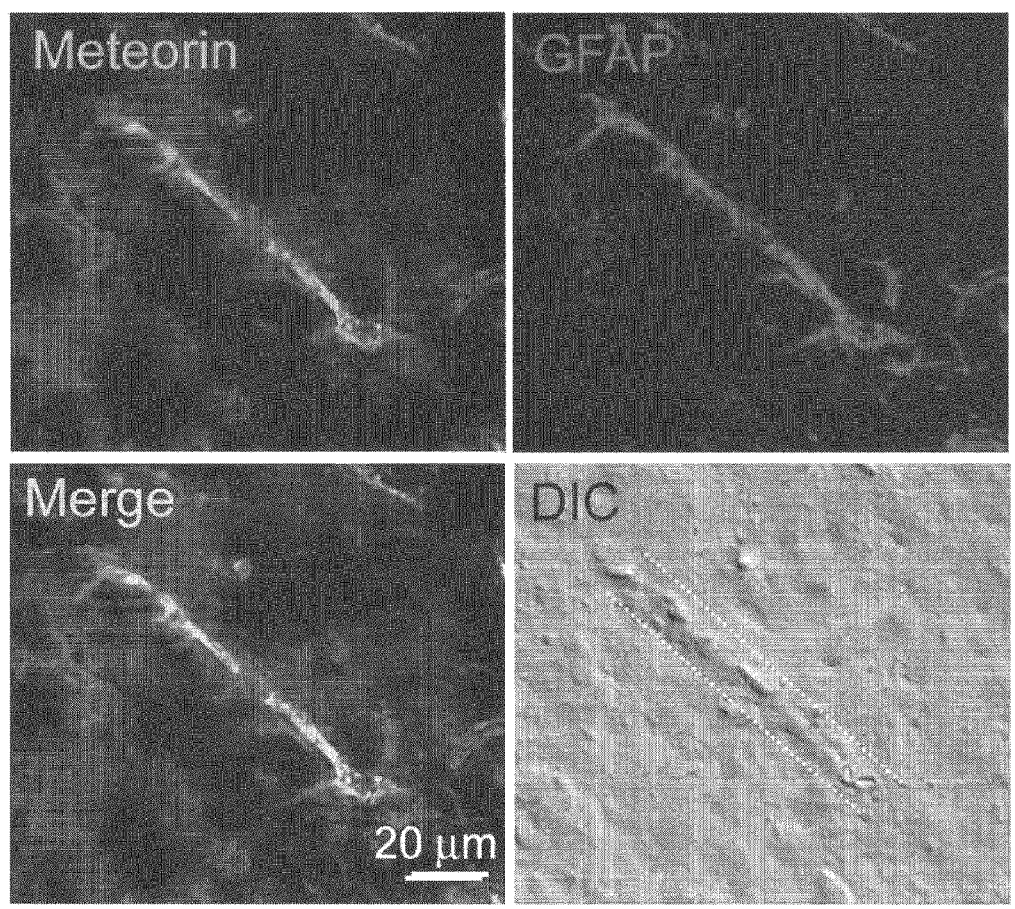

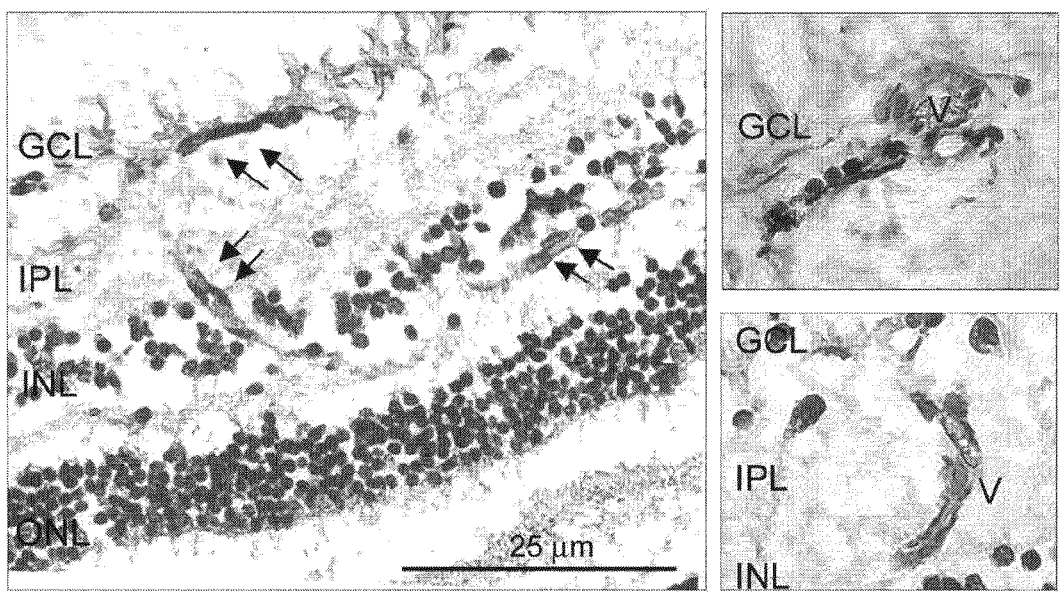
[Fig. 10]

[Fig. 11]
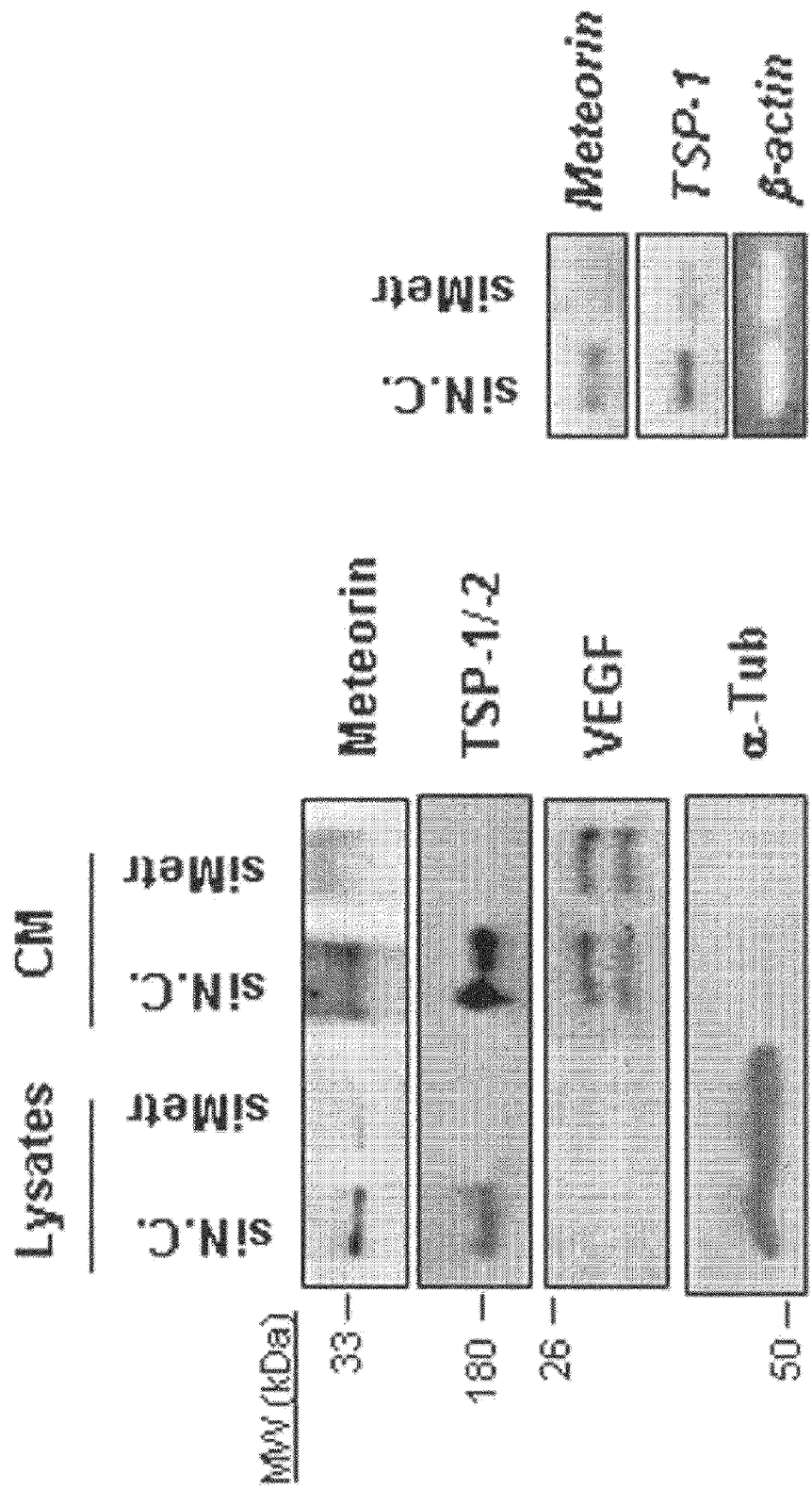

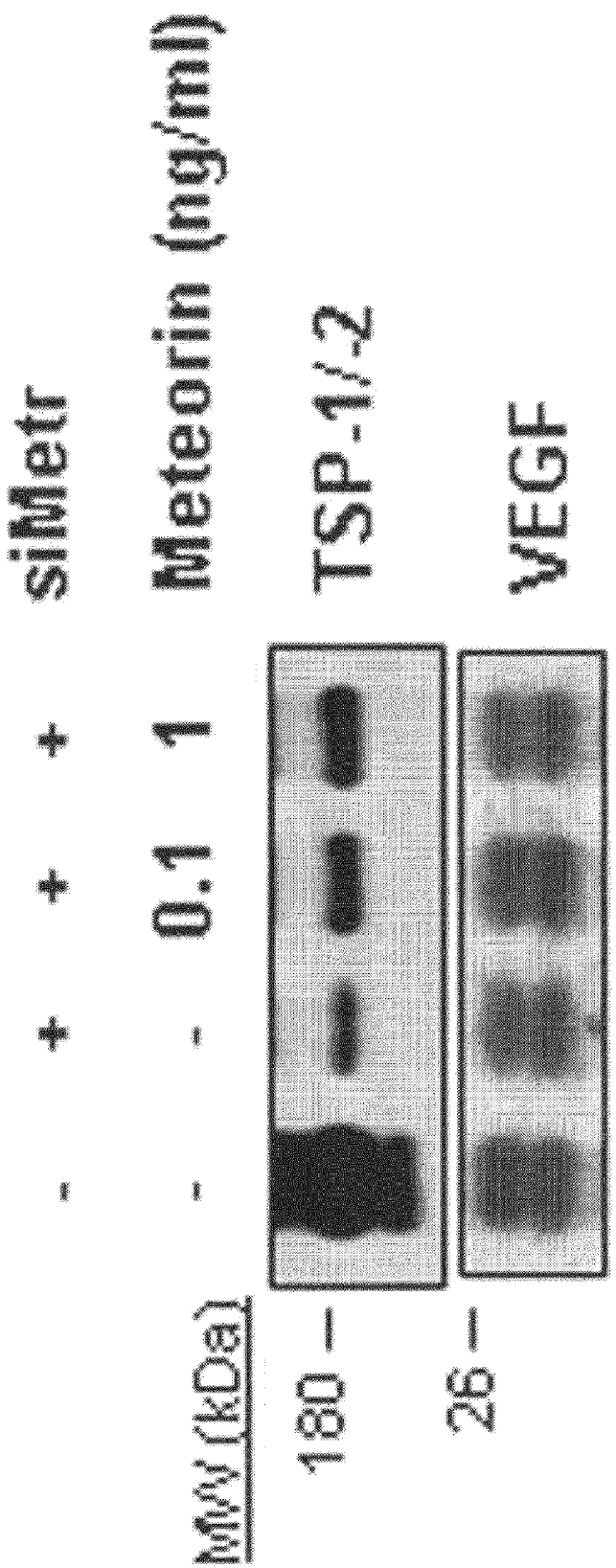
[Fig. 12]

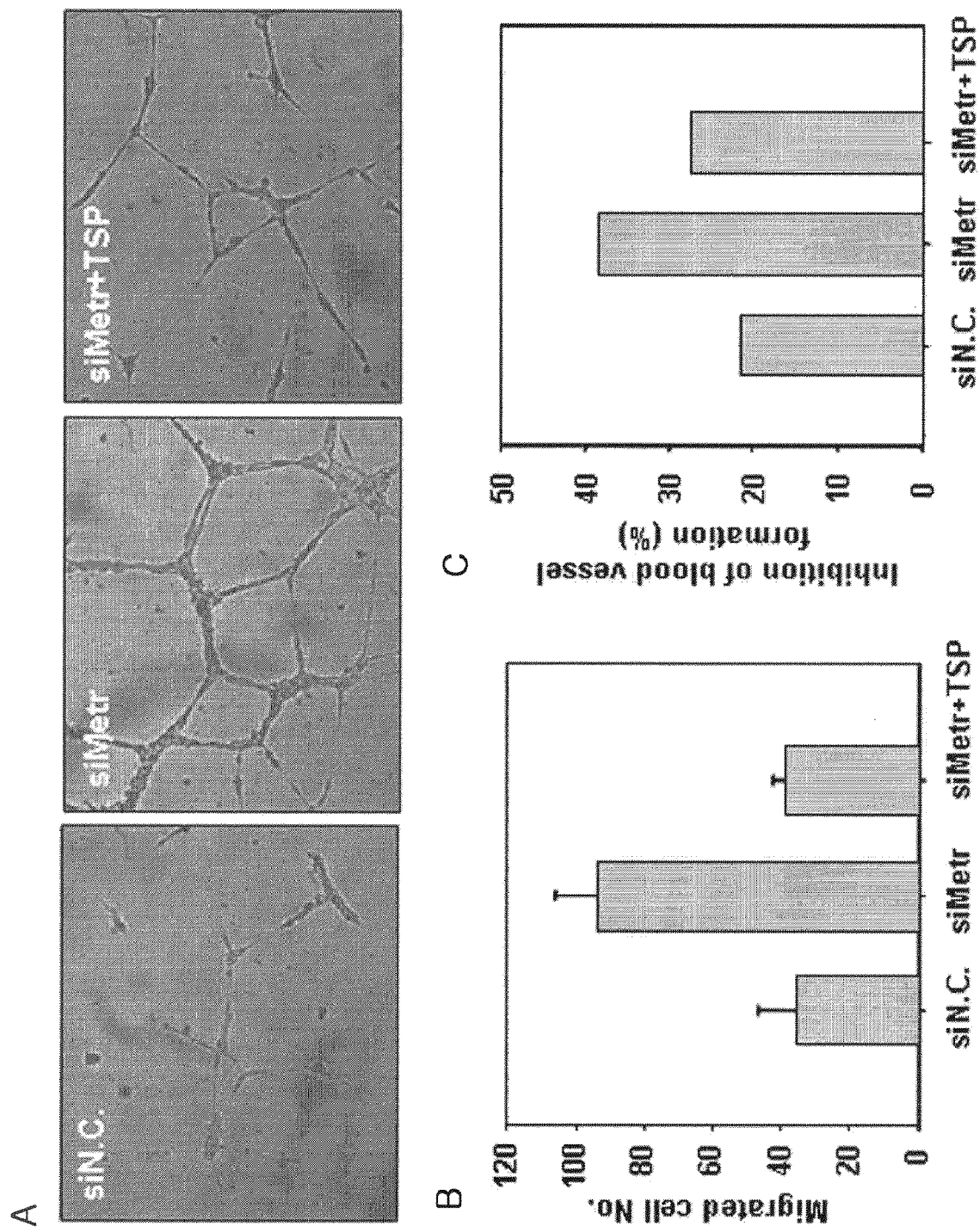
[Fig. 13]

[Fig. 14]
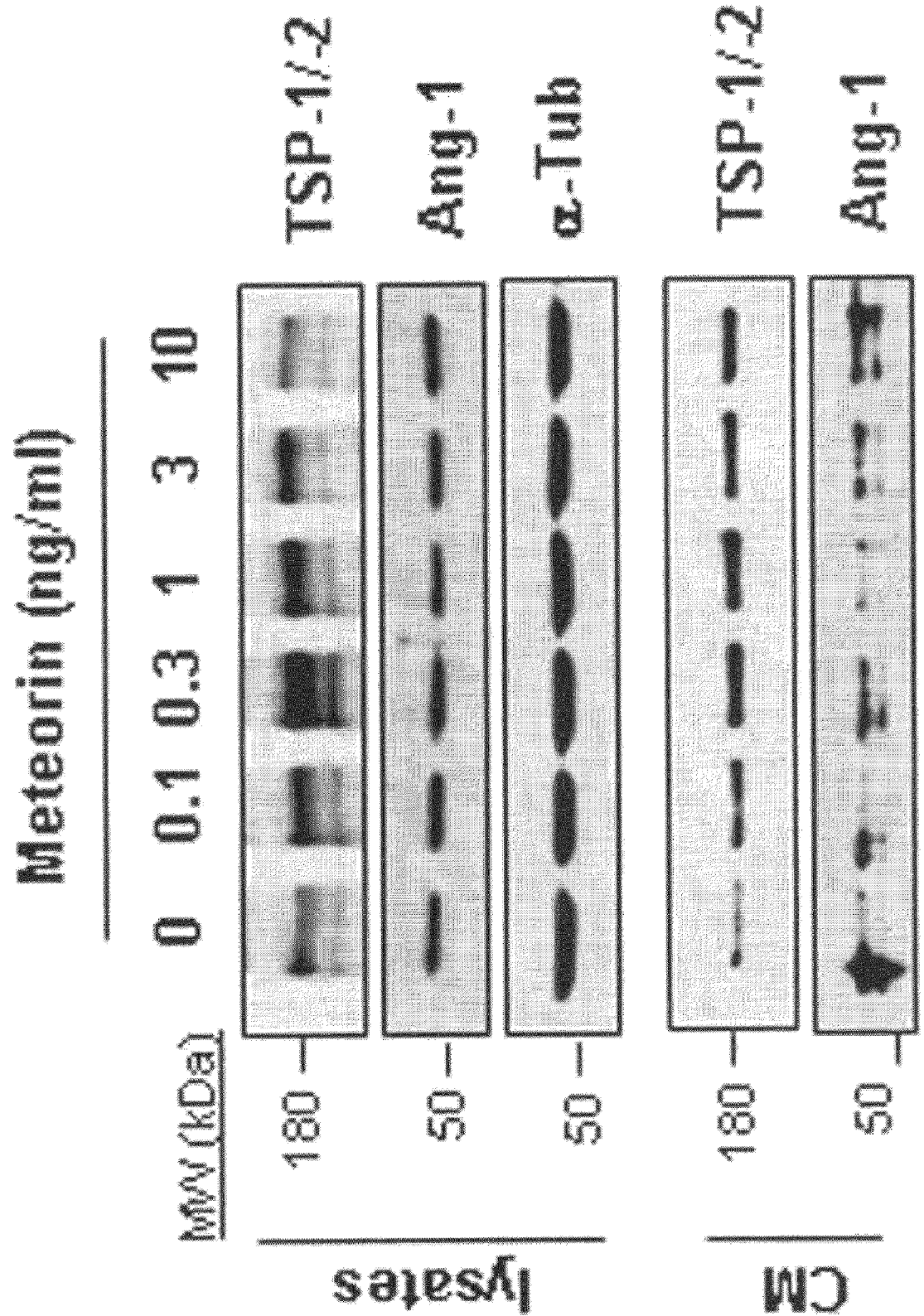

[Fig. 15]
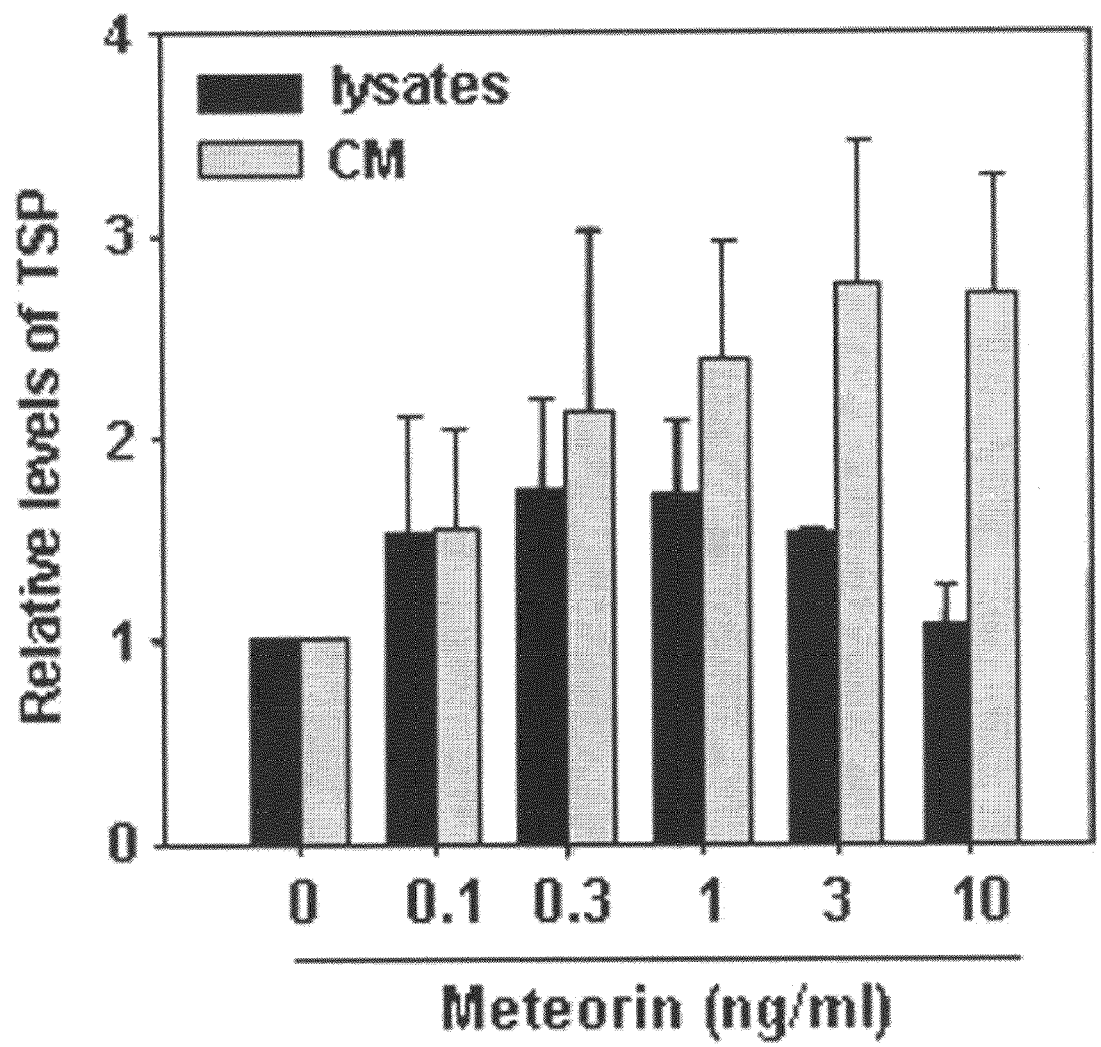

[Fig. 16]
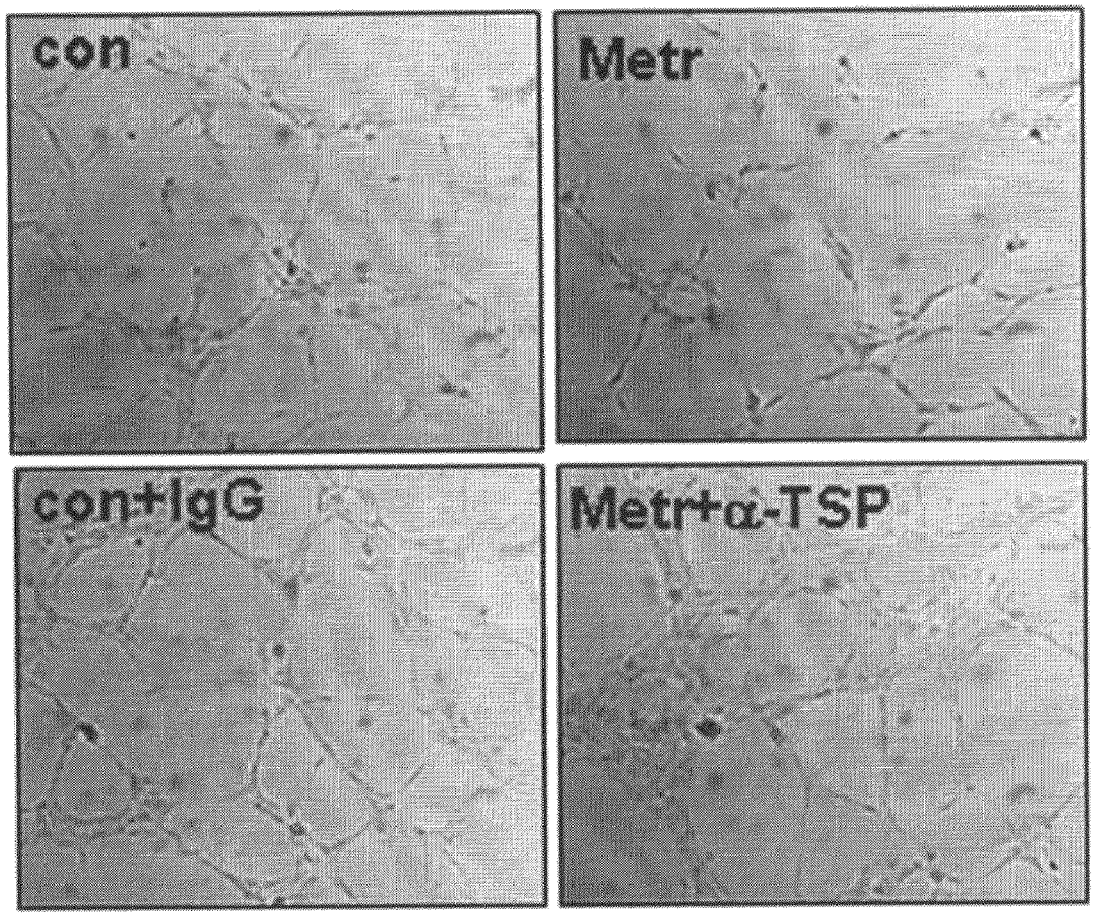

[Fig. 17]
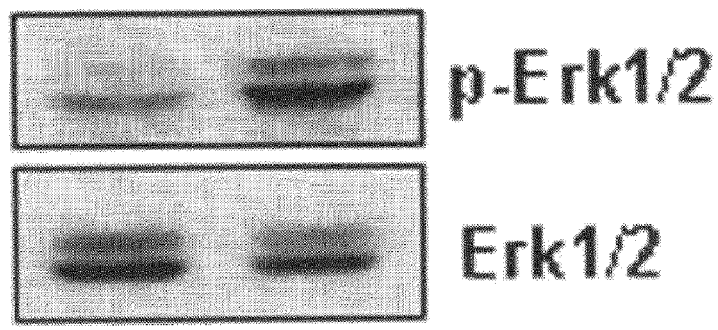

[Fig. 18]

SEQUENCE LISTING

<160> NUMBER OF SEQ ID NOS: 16

<210> SEQ ID NO 1
<211> LENGTH: 291

```
<212> TYPE: PRT
<213> ORGANISM: Rattus norvegicus

<400> SEQUENCE: 1

Met Leu Val Ala Ala Leu Leu Cys Ala Leu Cys Cys Gly Leu Leu Ala
1               5                   10                  15

Ala Ser Ala Arg Ala Gly Tyr Ser Glu Asp Arg Cys Ser Trp Arg Gly
            20                  25                  30

Ser Gly Leu Thr Gln Glu Pro Gly Ser Val Gly Gln Leu Thr Leu Asp
        35                  40                  45

Cys Thr Glu Gly Ala Ile Glu Trp Leu Tyr Pro Ala Gly Ala Leu Arg
50                  55                  60

Leu Thr Leu Gly Gly Ser Asp Pro Gly Thr Arg Pro Ser Ile Val Cys
65                  70                  75                  80

Leu Arg Pro Thr Arg Pro Phe Ala Gly Ala Gln Val Phe Ala Glu Arg
                85                  90                  95

Met Ala Gly Asn Leu Glu Leu Leu Ala Glu Gly Gln Gly Leu Ala
            100                 105                 110

Gly Gly Arg Cys Met Arg Trp Gly Pro Arg Glu Arg Ala Leu Phe
        115                 120                 125

Leu Gln Ala Thr Pro His Arg Asp Ile Ser Arg Arg Val Ala Ala Phe
130                 135                 140

Gln Phe Glu Leu His Glu Asp Gln Arg Ala Glu Met Ser Pro Gln Ala
145                 150                 155                 160

Gln Gly Phe Gly Val Asp Gly Ala Cys Arg Pro Cys Ser Asp Ala Glu
                165                 170                 175

Leu Leu Leu Thr Ala Cys Thr Ser Asp Phe Val Ile His Gly Thr Ile
            180                 185                 190

His Gly Val Val His Asp Met Glu Leu Gln Glu Ser Val Ile Thr Val
        195                 200                 205

Val Ala Thr Arg Val Ile Arg Gln Thr Leu Pro Leu Phe Gln Glu Gly
    210                 215                 220

Ser Ser Glu Gly Arg Gly Gln Ala Ser Val Arg Thr Leu Leu Arg Cys
225                 230                 235                 240

Gly Val Arg Pro Gly Pro Gly Ser Phe Leu Phe Met Gly Trp Ser Arg
                245                 250                 255

Phe Gly Glu Ala Trp Leu Gly Cys Ala Pro Arg Phe Gln Glu Phe Ser
            260                 265                 270

Arg Val Tyr Ser Ala Ala Leu Ala His Leu Asn Pro Cys Glu Val
        275                 280                 285

Ala Leu Asp
    290

<210> SEQ ID NO 2
<211> LENGTH: 924
<212> TYPE: PRT
<213> ORGANISM: Rattus norvegicus

<400> SEQUENCE: 2

Cys Cys Cys Cys Thr Ala Ala Cys Cys Ala Thr Gly Cys Thr Gly Gly
1               5                   10                  15

Thr Ala Gly Cys Gly Gly Cys Cys Thr Thr Cys Thr Cys Thr Gly
            20                  25                  30

Cys Gly Cys Gly Cys Thr Gly Thr Gly Cys Thr Gly Cys Gly Gly Cys
        35                  40                  45

Cys Thr Cys Thr Thr Gly Gly Cys Thr Gly Cys Gly Thr Cys Cys Gly
```

-continued

```
    50                  55                  60

Cys Thr Cys Gly Ala Gly Cys Thr Gly Gly Cys Thr Ala Cys Thr Cys
65                  70                  75                  80

Cys Gly Ala Gly Gly Ala Cys Cys Gly Cys Thr Gly Cys Ala Gly Cys
                85                  90                  95

Thr Gly Gly Ala Gly Gly Gly Gly Cys Ala Gly Cys Gly Gly Thr Thr
            100                 105                 110

Thr Gly Ala Cys Cys Cys Ala Gly Gly Ala Ala Cys Cys Thr Gly Gly
        115                 120                 125

Cys Ala Gly Cys Gly Thr Gly Gly Gly Gly Cys Ala Gly Cys Thr Gly
    130                 135                 140

Ala Cys Cys Cys Thr Gly Gly Ala Thr Thr Gly Thr Ala Cys Thr Gly
145                 150                 155                 160

Ala Gly Gly Gly Thr Gly Cys Thr Ala Thr Cys Gly Ala Gly Thr Gly
                165                 170                 175

Gly Cys Thr Gly Thr Ala Thr Cys Cys Ala Gly Cys Thr Gly Gly Gly
            180                 185                 190

Gly Cys Gly Cys Thr Gly Cys Gly Cys Cys Thr Gly Ala Cys Thr Cys
        195                 200                 205

Thr Ala Gly Gly Cys Gly Gly Cys Thr Cys Thr Gly Ala Thr Cys Cys
    210                 215                 220

Gly Gly Gly Cys Ala Cys Gly Cys Gly Gly Cys Cys Cys Ala Gly Cys
225                 230                 235                 240

Ala Thr Cys Gly Thr Cys Thr Gly Thr Cys Thr Gly Cys Gly Cys Cys
                245                 250                 255

Cys Ala Ala Cys Ala Cys Gly Gly Cys Cys Cys Thr Thr Cys Gly Cys
            260                 265                 270

Thr Gly Gly Thr Gly Cys Cys Cys Ala Gly Gly Thr Cys Thr Thr Cys
        275                 280                 285

Gly Cys Thr Gly Ala Ala Cys Gly Gly Ala Thr Gly Gly Cys Cys Gly
    290                 295                 300

Gly Cys Ala Ala Cys Cys Thr Ala Gly Ala Gly Thr Thr Gly Cys Thr
305                 310                 315                 320

Ala Cys Thr Gly Gly Cys Cys Gly Ala Ala Gly Gly Cys Cys Ala Ala
                325                 330                 335

Gly Gly Cys Cys Thr Gly Gly Cys Thr Gly Gly Gly Gly Gly Cys Cys
            340                 345                 350

Gly Cys Thr Gly Cys Ala Thr Gly Cys Gly Cys Thr Gly Gly Gly Gly
        355                 360                 365

Thr Cys Cys Thr Cys Gly Cys Gly Ala Gly Cys Gly Cys Cys Gly Ala
    370                 375                 380

Gly Cys Cys Cys Thr Thr Thr Thr Cys Cys Thr Gly Cys Ala Gly Gly
385                 390                 395                 400

Cys Cys Ala Cys Gly Cys Cys Ala Cys Ala Cys Cys Gly Gly Gly Ala
                405                 410                 415

Cys Ala Thr Cys Ala Gly Cys Cys Gly Cys Ala Gly Ala Gly Thr Thr
            420                 425                 430

Gly Cys Thr Gly Cys Cys Thr Thr Cys Cys Ala Ala Thr Thr Thr Gly
        435                 440                 445

Ala Ala Cys Thr Gly Cys Ala Cys Gly Ala Gly Gly Ala Cys Cys Ala
    450                 455                 460

Ala Cys Gly Thr Gly Cys Ala Gly Ala Ala Ala Thr Gly Thr Cys Thr
465                 470                 475                 480
```

-continued

```
Cys Cys Cys Cys Ala Gly Gly Cys Cys Cys Ala Ala Gly Gly Thr Thr
                485                 490                 495

Thr Thr Gly Gly Thr Gly Thr Gly Gly Ala Thr Gly Gly Thr Gly Cys
            500                 505                 510

Cys Thr Gly Cys Ala Gly Gly Cys Cys Cys Thr Gly Cys Ala Gly Thr
        515                 520                 525

Gly Ala Thr Gly Cys Cys Gly Ala Gly Cys Thr Cys Cys Thr Thr Cys
    530                 535                 540

Thr Gly Ala Cys Thr Gly Cys Ala Thr Gly Cys Ala Cys Cys Ala Gly
545                 550                 555                 560

Thr Gly Ala Cys Thr Thr Thr Gly Thr Gly Ala Thr Cys Cys Ala Thr
                565                 570                 575

Gly Gly Gly Ala Cys Cys Ala Thr Cys Cys Ala Thr Gly Gly Gly Gly
            580                 585                 590

Thr Cys Gly Thr Cys Cys Ala Thr Gly Ala Cys Ala Thr Gly Gly Ala
        595                 600                 605

Gly Cys Thr Gly Cys Ala Ala Gly Ala Ala Thr Cys Ala Gly Thr Cys
    610                 615                 620

Ala Thr Cys Ala Cys Thr Gly Thr Gly Gly Thr Gly Gly Cys Cys Ala
625                 630                 635                 640

Cys Thr Cys Gly Thr Gly Thr Cys Ala Thr Cys Cys Gly Cys Cys Ala
                645                 650                 655

Gly Ala Cys Ala Cys Thr Gly Cys Cys Ala Cys Thr Gly Thr Thr Cys
            660                 665                 670

Cys Ala Gly Gly Ala Ala Gly Gly Gly Ala Gly Cys Thr Cys Gly Gly
        675                 680                 685

Ala Gly Gly Gly Cys Cys Gly Gly Gly Gly Cys Cys Ala Gly Gly Cys
    690                 695                 700

Cys Thr Cys Cys Gly Thr Thr Cys Gly Thr Ala Cys Cys Thr Thr Gly
705                 710                 715                 720

Thr Thr Gly Cys Gly Cys Thr Gly Thr Gly Gly Thr Gly Thr Gly Cys
                725                 730                 735

Gly Thr Cys Cys Thr Gly Gly Cys Cys Cys Ala Gly Gly Cys Thr Cys
            740                 745                 750

Cys Thr Thr Cys Cys Thr Cys Thr Thr Cys Ala Thr Gly Gly Gly Cys
        755                 760                 765

Thr Gly Gly Ala Gly Cys Cys Gly Ala Thr Thr Thr Gly Gly Cys Gly
    770                 775                 780

Ala Ala Gly Cys Thr Thr Gly Gly Cys Thr Gly Gly Gly Cys Thr Gly
785                 790                 795                 800

Cys Gly Cys Thr Cys Cys Cys Cys Gly Cys Thr Thr Cys Cys Ala Ala
                805                 810                 815

Gly Ala Gly Thr Thr Cys Ala Gly Cys Cys Gly Thr Gly Thr Cys Thr
            820                 825                 830

Ala Thr Thr Cys Ala Gly Cys Thr Gly Cys Thr Cys Thr Cys Gly Cys
        835                 840                 845

Gly Gly Cys Cys Cys Ala Cys Cys Thr Cys Ala Ala Cys Cys Cys Ala
    850                 855                 860

Thr Gly Thr Gly Ala Gly Gly Thr Gly Gly Cys Ala Cys Thr Gly Gly
865                 870                 875                 880

Ala Cys Thr Gly Ala Gly Ala Gly Ala Cys Cys Thr Gly Gly Gly Ala
                885                 890                 895

Gly Cys Ala Ala Gly Cys Cys Cys Thr Gly Gly Ala Thr Gly Gly Ala
            900                 905                 910
```

```
Thr Cys Thr Thr Cys Cys Thr Cys Thr Gly Gly Gly
        915                 920
```

<210> SEQ ID NO 3
<211> LENGTH: 21
<212> TYPE: DNA
<213> ORGANISM: Artificial Sequence
<220> FEATURE:
<223> OTHER INFORMATION: mouse meteorin primer F

<400> SEQUENCE: 3
tccgctcacg ctggctactc g                                    21

<210> SEQ ID NO 4
<211> LENGTH: 22
<212> TYPE: DNA
<213> ORGANISM: Artificial Sequence
<220> FEATURE:
<223> OTHER INFORMATION: mouse meteorin primer R

<400> SEQUENCE: 4
gcagctctgt gtcatgggcg ac                                   22

<210> SEQ ID NO 5
<211> LENGTH: 16
<212> TYPE: DNA
<213> ORGANISM: Artificial Sequence
<220> FEATURE:
<223> OTHER INFORMATION: human meteorin primer F

<400> SEQUENCE: 5
atggggttcc cggccg                                          16

<210> SEQ ID NO 6
<211> LENGTH: 17
<212> TYPE: DNA
<213> ORGANISM: Artificial Sequence
<220> FEATURE:
<223> OTHER INFORMATION: human meteorin primer R

<400> SEQUENCE: 6
gtgcagcgcc acctcgc                                         17

<210> SEQ ID NO 7
<211> LENGTH: 20
<212> TYPE: DNA
<213> ORGANISM: Artificial Sequence
<220> FEATURE:
<223> OTHER INFORMATION: human TSP-1/-2 primer F

<400> SEQUENCE: 7
ctggacagct catcacagga                                      20

<210> SEQ ID NO 8
<211> LENGTH: 20
<212> TYPE: DNA
<213> ORGANISM: Artificial Sequence
<220> FEATURE:
<223> OTHER INFORMATION: human TSP-1/-2 primer R

<400> SEQUENCE: 8
ttgtctttgg aaccacacca                                      20

<210> SEQ ID NO 9
<211> LENGTH: 18
<212> TYPE: DNA

<213> ORGANISM: Artificial Sequence
<220> FEATURE:
<223> OTHER INFORMATION: b actin primer F

<400> SEQUENCE: 9
gactacctca tgaagatc                                                 18

<210> SEQ ID NO 10
<211> LENGTH: 18
<212> TYPE: DNA
<213> ORGANISM: Artificial Sequence
<220> FEATURE:
<223> OTHER INFORMATION: b actin primer R

<400> SEQUENCE: 10
gatccacatc tgctggaa                                                 18

<210> SEQ ID NO 11
<211> LENGTH: 293
<212> TYPE: PRT
<213> ORGANISM: Homo sapiens

<400> SEQUENCE: 11

```
Met Gly Phe Pro Ala Ala Ala Leu Leu Cys Ala Leu Cys Cys Gly Leu
1               5                  10                  15

Leu Ala Pro Ala Ala Arg Ala Gly Tyr Ser Glu Glu Arg Cys Ser Trp
            20                  25                  30

Arg Gly Ser Gly Leu Thr Gln Glu Pro Gly Ser Val Gly Gln Leu Ala
        35                  40                  45

Leu Ala Cys Ala Glu Gly Ala Val Glu Trp Leu Tyr Pro Ala Gly Ala
    50                  55                  60

Leu Arg Leu Thr Leu Gly Gly Pro Asp Pro Arg Ala Arg Pro Gly Ile
65                  70                  75                  80

Ala Cys Leu Arg Pro Val Arg Pro Phe Ala Gly Ala Gln Val Phe Ala
                85                  90                  95

Glu Arg Ala Gly Gly Ala Leu Glu Leu Leu Ala Glu Gly Pro Gly
            100                 105                 110

Pro Ala Gly Gly Arg Cys Val Arg Trp Gly Pro Arg Glu Arg Arg Ala
        115                 120                 125

Leu Phe Leu Gln Ala Thr Pro His Gln Asp Ile Ser Arg Arg Val Ala
    130                 135                 140

Ala Phe Arg Phe Glu Leu Arg Glu Asp Gly Arg Pro Glu Leu Pro Pro
145                 150                 155                 160

Gln Ala His Gly Leu Gly Val Asp Gly Ala Cys Arg Pro Cys Ser Asp
                165                 170                 175

Ala Glu Leu Leu Leu Ala Ala Cys Thr Ser Asp Phe Val Ile His Gly
            180                 185                 190

Ile Ile His Gly Val Thr His Asp Val Glu Leu Gln Glu Ser Val Ile
        195                 200                 205

Thr Val Val Ala Ala Arg Val Leu Arg Gln Thr Pro Pro Leu Phe Gln
    210                 215                 220

Ala Gly Arg Ser Gly Asp Gln Gly Leu Thr Ser Ile Arg Thr Pro Leu
225                 230                 235                 240

Arg Cys Gly Val His Pro Gly Pro Gly Thr Phe Leu Phe Met Gly Trp
                245                 250                 255

Ser Arg Phe Gly Glu Ala Arg Leu Gly Cys Ala Pro Arg Phe Gln Glu
            260                 265                 270

Phe Arg Arg Ala Tyr Glu Ala Ala Arg Ala Ala His Leu His Pro Cys
```

Glu Val Ala Leu His
            290

<210> SEQ ID NO 12
<211> LENGTH: 1109
<212> TYPE: DNA
<213> ORGANISM: Homo sapiens

<400> SEQUENCE: 12

| | | | | | |
|---|---|---|---|---|---|
| gcttcgccgg | ggccgggcgg | ccggcgcccc | cggctgctcc | cgccgccgcc | cggacccgcg | 60 |
| ccccgccggg | gcagcggtgg | tgagagcccc | gactccccgg | acgccgcccg | ccgtgccatg | 120 |
| gggttcccgg | ccgcggcgct | gctctgcgcg | ctgtgctgcg | gcctcctggc | cccggctgcc | 180 |
| cgcgccggct | actccgagga | gcgctgcagc | tggaggggca | gcggcctcac | ccaggagccc | 240 |
| ggcagcgtgg | ggcagctggc | cctggcctgt | gcggagggcg | cggttgagtg | gctgtacccg | 300 |
| gctggggcgc | tgcgcctgac | cctgggcggc | cccgatccca | gagcgcggcc | cggcatcgcc | 360 |
| tgtctgcggc | cggtgcggcc | cttcgcgggc | gcccaggtct | tcgcggagcg | cgcagggggc | 420 |
| gccctggagc | tgctgctggc | cgagggcccc | ggccccgcag | ggggccgctg | cgtgcgctgg | 480 |
| ggtccccgcg | agcgccgggc | cctcttcctg | caggccacgc | cgcaccagga | catcagccgc | 540 |
| cgcgtggccc | ccttccgctt | tgagctgcgc | gaggacgggc | gccccgagct | gccccgcag | 600 |
| gcccacggtc | tcggcgtaga | cggtgcctgc | aggccctgca | gcgacgctga | gctgctcctg | 660 |
| gccgcatgca | ccagcgactt | cgtaattcac | gggatcatcc | atggggtcac | ccatgacgtg | 720 |
| gagctgcagg | agtctgtcat | cactgtggtg | gccgcccgtg | tcctccgcca | gacaccgccg | 780 |
| ctgttccagg | cggggcgatc | cggggaccag | gggctgacct | ccattcgtac | cccactgcgc | 840 |
| tgtggcgtcc | acccgggccc | aggcaccttc | ctcttcatgg | gctggagccg | ctttggggag | 900 |
| gcccggctgg | gctgtgcccc | acgattccag | gagttccgcc | gtgcctacga | ggctgcccgt | 960 |
| gctgcccacc | tccacccctg | cgaggtggcg | ctgcactgag | gggctgggtg | ctggggaggg | 1020 |
| gctggtagga | gggagggtgg | gcccactgct | ttggaggtga | tgggactatc | aataagaact | 1080 |
| ctgttcacgc | aaaaaaaaaa | aaaaaaaaa | | | | 1109 |

<210> SEQ ID NO 13
<211> LENGTH: 19
<212> TYPE: RNA
<213> ORGANISM: Artificial Sequence
<220> FEATURE:
<223> OTHER INFORMATION: meteorin siRNA

<400> SEQUENCE: 13
cugcaggagu cugucauca                                                  19

<210> SEQ ID NO 14
<211> LENGTH: 291
<212> TYPE: PRT
<213> ORGANISM: Mus musculus

<400> SEQUENCE: 14

Met Leu Val Ala Thr Leu Leu Cys Ala Leu Cys Cys Gly Leu Leu Ala
1               5                   10                  15

Ala Ser Ala His Ala Gly Tyr Ser Glu Asp Arg Cys Ser Trp Arg Gly
            20                  25                  30

Ser Gly Leu Thr Gln Glu Pro Gly Ser Val Gly Gln Leu Thr Leu Asp
        35                  40                  45

```
Cys Thr Glu Gly Ala Ile Glu Trp Leu Tyr Pro Ala Gly Ala Leu Arg
 50                  55                  60

Leu Thr Leu Gly Gly Pro Asp Pro Gly Thr Arg Pro Ser Ile Val Cys
 65                  70                  75                  80

Leu Arg Pro Glu Arg Pro Phe Ala Gly Gln Val Phe Ala Glu Arg
                 85                  90                  95

Met Thr Gly Asn Leu Glu Leu Leu Ala Glu Gly Pro Asp Leu Ala
                100                 105                 110

Gly Gly Arg Cys Met Arg Trp Gly Pro Arg Glu Arg Ala Leu Phe
            115                 120                 125

Leu Gln Ala Thr Pro His Arg Asp Ile Ser Arg Val Ala Ala Phe
    130                 135                 140

Arg Phe Glu Leu His Glu Asp Gln Arg Ala Glu Met Ser Pro Gln Ala
145                 150                 155                 160

Gln Gly Leu Gly Val Asp Gly Ala Cys Arg Pro Cys Ser Asp Ala Glu
                165                 170                 175

Leu Leu Leu Ala Ala Cys Thr Ser Asp Phe Val Ile His Gly Thr Ile
                180                 185                 190

His Gly Val Ala His Asp Thr Glu Leu Gln Glu Ser Val Ile Thr Val
            195                 200                 205

Val Val Ala Arg Val Ile Arg Gln Thr Leu Pro Leu Phe Lys Glu Gly
    210                 215                 220

Ser Ser Glu Gly Gln Gly Arg Ala Ser Ile Arg Thr Leu Leu Arg Cys
225                 230                 235                 240

Gly Val Arg Pro Gly Pro Gly Ser Phe Leu Phe Met Gly Trp Ser Arg
                245                 250                 255

Phe Gly Glu Ala Trp Leu Gly Cys Ala Pro Arg Phe Gln Glu Phe Ser
                260                 265                 270

Arg Val Tyr Ser Ala Ala Leu Thr Thr His Leu Asn Pro Cys Glu Met
            275                 280                 285

Ala Leu Asp
    290

<210> SEQ ID NO 15
<211> LENGTH: 1363
<212> TYPE: DNA
<213> ORGANISM: Mus musculus

<400> SEQUENCE: 15
gggcagccgc gccgcgggct gctcgcgctg cggccccgac cctcccgggg cagcagtccg    60
aggccccggc gcgtccccta accatgctgg tagccacgct tctttgcgcg ctctgttgcg   120
gcctcctggc cgcgtccgct cacgctggct actcggaaga ccgctgcagc tggaggggca   180
gcggttttga ccaggagcct ggcagcgtgg ggcagctgac cctggactgt actgagggcg   240
ctatcgagtg gctgtaccca gctggggcgc tgcgcctgac cctgggcggc ccgatccgg   300 gcacacggcc cagcatcgtc tgtctgcgcc cagagcggcc cttcgctggt gcccaggtct   360
tcgctgaacg tatgaccggc aatctagagt tgctactggc cgagggcccg acctggctg    420 ggggccgctg catgcgctgg ggtccccgcg agcgccgagc cctttttcctg caggccacac   480 cacaccgcga catcagccgc agagttgctg ccttccgttt tgaactgcac gaggaccaac   540
gtgcagaaat gtctccccag gctcaaggtc ttggtgtgga tggtgcctgc aggccctgca   600
gtgatgccga gctcctcctg gctgcatgca ccagtgattt tgtgatccac gggaccatcc   660
atggggtcgc ccatgacaca gagctgcaag aatcagtcat cactgtggtg gttgctcgtg   720
```

```
tcatccgcca gacactgcca ctgttcaagg aagggagctc ggagggccaa ggccgggcct    780
ccattcgtac cttgctgcgc tgtggtgtgc gtcctggccc aggctccttc ctcttcatgg    840
gctggagccg atttggcgaa gcttggctgg gctgtgctcc ccgcttccaa gagttcagcc    900
gtgtctattc agctgctctc acgacccatc tcaacccatg tgagatggca ctggactgag    960
agacctggga gcaagccctg gatggacctt cttctggaga tggggtgttg gggagggtga   1020
tgggagggtg ggtgagaagg gtgtggctcg gatggcatcc tggtacccac agtgagctgg   1080
tagaatacta agtaatctgg accataccag ccactgtagt catggtcttc tgtggcaggc   1140 agcatacccca gctctgtgcc tgcctcactt tgtctactct ccagtctgct gcccttctaa   1200
cccttcttag cctgctgacc agtgagctca tgttttcctc gaattccagg gtgctgctgg   1260
ggttcagagc aaccgtgccg tagtttggaa gacttgagct aattgttttt tttttgtttg   1320 ttttttttgtt tgtttaaagg tggcctgggg ggggcggcaa aca                   1363

<210> SEQ ID NO 16
<211> LENGTH: 21
<212> TYPE: RNA
<213> ORGANISM: Artificial Sequence
<220> FEATURE:
<223> OTHER INFORMATION: meteorin siRNA

<400> SEQUENCE: 16
aacugcagga gucugucauc a                                              21
```

ANGIOGENESIS INHIBITOR COMPRISING METEORIN AS AN ACTIVE INGREDIENT

CROSS-REFERENCE TO RELATED APPLICATIONS

This application is the U.S. National Stage of International Application No. PCT/KR2007/002146, filed May 2, 2007 and published in English on Nov. 13, 2008 as WO 2008/136541, all of which are hereby incorporated by reference in their entirety to the extent not inconsistent with the disclosure herein.

TECHNICAL FIELD

The present invention relates to a method of treating or preventing angiogenesis related diseases comprising administrating a meteorin as an active ingredient via autocrine pathway and thus inhibits angiogenesis.

BACKGROUND ART

The blood vessels of the central nervous system are enveloped by a basement membrane surrounded by astrocyte spurs stretched toward the endothelial cell barrier (Risau, W., Nature 386, 671-674, 1997; Abbott, N. J., et al., Nat. Rev. Neurosci. 7, 41-53, 2006; Kim, J. H., et al., J. Biochem. Mol. Biol. 39, 339-345, 2006; Ballabh, P., et al., Neurobiol. Dis. 16, 1-13, 2004). The endothelial cell barrier has a highly selective permeability and plays an important role in regulating the homeostasis of the micro-environment in the brain. This structure is called the gliovascular interface (Abbott, N. J., et al., Nat. Rev. Neurosci. 7, 41-53, 2006). Structural change of the gliovascular interface is observed when a pathological status of the central nervous system, including ischemia or neuroglyoma develops. This structural change includes phenomena such as atrocytes falling apart from the blood vessel where abnormal angiogenesis occurs and where the blood leaks (Rich, J. N., and Bigner, D. D Nat. Rev. Drug Discov. 3, 430-446, 2004; Maher, E. A., Genes Dev. 15, 1311-1333, 2001; Lee, S. W., et al., Arch. Pharm. Res. 29, 265-275, 2006). Thus, the interaction between astrocytes and endothelial cells is a key factor for regulating the barrier in the gliovascular interface. However, the exact mechanism of regulating this interaction has not been fully explained.

According to recent reports, neovascularization in the central nervous system can be explained by two important mechanisms: angiogenesis and barriergenesis (Lee, S. W., et al., Nat. Med. 9, 900-906, 2003; Rieckmann, P. and Engelhardt, B Nat. Med. 9, 828-829, 2003; Park, J. A., et al., Ontogeny to Artificial Interfaces, pp. 41-59, 2006). Particularly, astroglial cells of the brain and retina under development recognize the hypoxia generated in neuroglial cells to induce angiogenesis (Risau, W., Nature 386, 671-674, 1997). The newly generated blood vessels become mature as development proceeds. Angiogenesis then stops and the endothelial cells of the blood vessels gain selective permeability via barriergenesis (Engelhardt, B., Cell Tissue Res. 314, 119-129, 2003; Riasu, W. and Wolburg, H. Trends Neurosci. 13, 174-178, 1990). A few previous studies have found that the endothelial cells and astrocytes interact to induce the maturation of blood vessels and maintain the matured blood vessels that have barrier characteristics in the gliovascular interface (Risau, W., Proc. Natl. Acad. Sci. U.S.A. 83, 3855-3859, 1986; Janzer, R. C. and Raff, M. C. Nature 325, 253-257, 1987; Laterra, J., et al., J. Cell Physiol. 144, 204-215, 1990; Zerlin, M. and Goldman, J. E. J. Comp Neurol. 387, 537-546, 1997).

Astrocytes in the gliovascular interface have been known to play an important role in regulating the growth, stabilization and maturation of blood vessels. That is, the astrocytes regulate the expression and secretion of various factors needed to build a functional blood vessel (Risau, W., Proc. Natl. Acad. Sci. U.S.A. 83, 3855-3859, 1986; Yonezawa, T., et al., Glia 44, 190-204, 2003; Haseloff, R. F., et al., Cell Mol. Neurobiol. 25, 25-39, 2005; Chow, J., et al., Brain Res. Dev. Brain Res. 130, 123-132, 2001; West, H., et al., Development 132, 1855-1862, 2005). Under the influence of a local factor, endothelial cells of the blood vessel become tighter and form wider intercellular junctions.

The present inventors investigated gene expression in relation to oxygen regulation in astrocytes to study astrocyte-mediated signals involved in blood vessel maturation and confirmed that this mechanism is closely related to angiogenesis (Lee, S. W., et al., Nat. Med. 9, 900-906, 2003; Song, H. S., et al., Biochem. Biophys. Res. Commun. 290, 325-331, 2002). According to the previous study, the oxygen regulating gene (hyrac; PubMed Access No. AY800384 and DQ133462) separated from the astrocytes of the brain after the birth of a rat encodes meteorin protein (Nishino, J. et al., EMBO J. 23, 1998-2008, 2004). Particularly, meteorin is a secreted protein, which is expressed in non-differentiated neural precursor cells and radial glia. Meteorin indirectly promotes the axon extension in the presence of astrocytes. In this study, the indirect effect of meteorin on neurons is presumably attributed to environmental changes that provide a signal for nerve growth.

The present inventors completed this invention by confirming that meteorin is highly expressed in astrocytes of the brain and retina of a mouse in the late embryonic stage and right after birth. It is in particular highly detected in the astrocyte endfeet surrounding blood vessels, and promotes the expression of thrombospondin-1/-2 (TSP-1/-2) to inhibit angiogenesis and accelerate blood vessel maturation.

DISCLOSURE

Technical Problem

A goal of the present invention is to provide a method of treating or preventing angiogenesis related disease comprising meteorin as an active ingredient.

Technical Solution

A method of inhibiting angiogenesis administrating a meteorin to a subject in need thereof in a pharmaceutically effective amount. The present invention provides a method of preventing and treating of an angiogenesis-related disease comprising administrating a meteorine to a subject in need thereof in a pharmaceutically effective amount for inhibiting angiogenesis in the subject that comprises meteorin as an active ingredient for the prevention and treatment of angiogenesis related diseases including cerebrovascular disease, cardiovascular disease, ocular disease and cancer.

In the following, the present invention is described in detail.

To isolate oxygen-controlling gene from rat astrocytes, the present inventors performed RDA (representative difference complementary DNA assay) to confirm ESTs (expressed sequence tags) in the rat which increased during reoxygenation after hypoxia. Based on the EST sequences, the present inventors performed RACE PCR (rapid amplification of cDNA ends PCR) to determine the total length of the complementary DNA, which was then named as Hyrac (hypoxia/ reoxygenation regulatory factor in astrocytes, PubMed Access No. AY800384). The Hyrac was identified as meteorin by Nishino et al (*EMBO J.* 23, 1998-2008, 2004), so in the present invention it was used in the name of "meteorin (SEQ. ID. NO: 1 and NO: 2)".

Since meteorin gene encodes secretion signal domain, CHO (Chinese hamster ovary) cells were transfected with the meteorin gene by using lipofectamin (Invitrogen, USA) and then selection was made by geneticin (GibcoBRL, USA), resulting in the establishment of the stable meteorin cell line. Meteorin protein secreted from the cell line was purified (see FIG. 1) and the purified protein was preferably concentrated and dialyzed.

Meteorin of the present invention is selected from the group consisting of:

(a) a protein comprising the amino acid sequence of SEQ. ID. NO: 1, No: 11 or No: 14;

(b) a protein encoded by the DNA comprising the coding region of the nucleotide sequence of SEQ. ID. NO: 2, NO: 12 or NO: 15;

(c) a protein that is functionally same as the protein comprising the amino acid sequence of SEQ. ID. NO: 1, NO: 11 or NO: 14 and composed of the amino acid sequence with the modification by substitution, deletion, insertion and/or addition of one or more amino acids from the amino acid sequence of SEQ. ID. NO: 1, NO: 11 or NO: 14; and (d) a protein encoded by the DNA hybridized with the DNA comprising the nucleotide sequence of SEQ. ID. NO: 2, NO: 12 or NO: 15 under strict conditions or a protein that is functionally identical to the protein comprising the amino acid sequence of SEQ. ID. NO: 1, NO: 11 or NO: 14.

Hybridization under strict conditions favors the selection of DNA having a highly homologous nucleotide sequence, so that the resultant separated protein is functionally equal to meteorin. The 'highly homologous nucleotide sequence' above indicates that the sequence has at least 70% homology, preferably at least 80% homology, more preferably at least 90% homology, and most preferably at least 95% homology with the nucleotide sequence represented by SEQ. ID. NO: 2, NO: 12 or NO: 15. Any amino acid sequence that has at least 70% homology, preferably at least 80% homology, more preferably at least 90% homology and most preferably at least 95% homology with the amino acid sequence represented by SEQ. ID. NO: 1, NO: 11 or NO: 14 can be used. The homology ratio can be determined by the conventional algorithm selected by experts in the field.

The hybridization can be performed by DNA-DNA hybridization under strict conditions set by experts in the field (Hames and Higgins, Eds. Nucleic Acid Hybridization, IRL Press, U.K., 1985).

The strict conditions for hybridization are applied to the washing process; for example, a 15 minutes wash with 6×SSC, 0.5% SDS at room temperature, followed by a 30 minutes wash with 2×SSC, 0.5% SDS at 45° C., followed by two 30 minute washes with 0.2×SSC, 0.5% SDS at 50° C. It is more preferable to wash at a higher temperature. At this time, the last two 30 minute washes are performed with 0.2× SSC, 0.5% SDS at 60° C. but the previous wash is performed by the same conditions as the above. Another strict condition is that the last two washes are performed at 65° C. with 0.1×SSC, 0.1% SDS. It is well understood by experts in the field that necessary conditions can be properly determined.

Furthermore, the meteorin of the present invention can be any meteorin derived from mammalia, but is preferably rat derived meteorin, represented by SEQ. ID. NO: 1, human derived meteorin represented by SEQ. ID. NO: 11 or mouse derived meteorin represented by SEQ. ID. NO: 14. The mammalian meteorin is exemplified by human, mouse, rat, guinea pig, rabbit, pig, sheep, goat, dog, cow, monkey and chimpanzee.

The concentration of Meteorin was significantly increased under reoxygenation of astrocytes after hypoxia (see FIG. 2), suggesting that meteorin is a protein whose expression is regulated by oxygen level.

Meteorin expression was significant particularly in the brain, compared with the expression in any other organ (see FIG. 3), suggesting that meteorin is a protein largely located in the brain.

Meteorin expression is greater in the brain of mice in the embryonic stage than in the brain after birth. Even though meteorin is detected in the brain after birth or in the adult brain, the expression decreases slightly as brain development continues (see FIG. 4), indicating that meteorin is an essential protein for brain development.

Meteorin immune response was observed in every region of the cerebrum cortex in the mouse on the $7^{th}$ day after birth (see FIG. 5), and the expression could be detected in blood vessels with a star-shape structure. A similar meteorin immune response was observed in the hippocampus (see FIG. 6). The above results indicate that meteorin immune response in star-shaped astrocytes is closely associated with blood vessels.

Meteorin is not expressed in pericytes and endothelial cells (see FIG. 7 and FIG. 8), but meteorin immune response and GFAP immune response are equally distributed in astrocytes (GFAP) (see FIG. 9). This equal distribution is related to blood vessels, and meteorin is precisely expressed in astrocytes that directly contact with blood vessels during angiogenesis and barriergenesis.

As explained before, the expression of meteorin depends on oxygen dose, specifically in astrocytes around blood vessels, and affects blood vessel differentiation via paracrine pathway and thus contributes to the function of the endothelial cell barrier.

Meteorin immune response is detected in GCL (ganglion cell layer), IPL (innerplexiform layer) and INL (inner nuclear layer) on the $39^{th}$ week of the human embryo when the selective barrier of the blood vessel is formed (see FIG. 10).

According to recent reports, meteorin induces the expression of other releasing factors to indirectly promote axonal extension and to directly increase glial differentiation (Nishino, J., et al., *EMBO J.* 23, 1998-2008, 2004). Thus, the present inventors investigated whether meteorin derived from astrocytes could affect angiogenesis by inducing various signal factors involved in angiogenesis.

First, endogenous meteorin expression in astrocytes was suppressed by meteorin siRNA. The suppression of meteorin expression was confirmed by the examination of cell lysates and conditioned medium (see FIG. 11, left). When endogenous meteorin expression was suppressed by siRNA, TSP-1/-2 expression and secretion in astrocytes was reduced but VEGF (vascular endothelial growth factor) expression was not changed.

Suppression of meteorin expression was also confirmed by investigating mRNA level. This examination revealed that TSP-1/-2 mRNA level was also reduced (see FIG. 11, right).

To make sure that the decrease of mRNA was not due to the siRNA itself, the present inventors treated astrocytes exposed to meteorin siRNA with purified meteorin protein. As a result, TSP-1/-2 expression was recovered in the astrocytes (see FIG. 12). This result indicates that it is meteorin what regulates TSP-1/-2 expression and secretion in astrocytes.

The TSP protein is a glycoprotein expressed and secreted in cells (Adams, J. C., *Annu. Rev. Cell Dev. Biol.* 17, 25-5, 2001). In particular, TSP-1/-2 acts as an angiogenesis inhibitor that inhibits tube formation and migration of endothelial cells via the CD36 receptor.

Therefore, meteorin can inhibit angiogenesis by increasing TSP-1/-2 expression.

Next, the conditioned medium (siMetr-ACM) obtained from astrocytes transfected with meteorin siRNA was treated to human brain microvascular endothelial cells (HBMEC). As a result, tube formation, migration of microvascular endothelial cells and expression of CAM (chorioallantoic membrane) were increased (see FIG. 13).

The treatment of siMetr-ACM and TSP protein inhibited angiogenesis (see FIG. 13, siMetr+TSP). The above result indicates that meteorin secreted in the medium induces TSP-1/-2 expression and secretion via autocrine pathway and thus meteorin can indirectly inhibit angiogenesis by regulating TSP-1/-2 level in astrocytes.

To investigate the mechanism of TSP expression induced by meteorin, different concentrations of meteorin were treated to human astrocytes and then the level of TSP-1/-2 was measured. As a result, TSP-1/-2 level increased meteorin dose-dependently but the level of angiopoietin-1 did not change (see FIG. 14 and FIG. 15).

The present inventors also investigated the effect of meteorin on tube formation. When HBMEC was exposed to the conditioned medium from astrocytes treated with meteorin (Metr-ACM), tube formation was inhibited (see FIG. 16). This result indicates that meteorin could function as an angiogenesis inhibitor. To prove the presumption that the angiogenesis inhibiting effect resulted from TSP-1/-2, the present inventors used a neutralizing antibody that inhibited TSP activity. This antibody prevented TSP from binding to the CD36 receptor and thus inhibited TSP-1/-2 activity. Co-treatment with the neutralizing antibody to TSP-1/-2 nullified the antiangiogenic activity (see FIG. 16, Metr-+α-TSP), suggesting that TSP-1/-2 of Metr-ACM mediated the antiangiogenic activity.

It has been recently reported that the activation of ERK1/2 and Akt1 pathway contributes to the expression of TSP-1/-2. The present inventors discovered that Erk1/2 phosphorylation was induced when meteorin protein was treated to astrocytes (see FIG. 17, upper part). When MEK [Mitogen-Activated Protein (MAP) Kinase] inhibitor U0126 and meteorin was treated stepwise to astrocytes, TSP-1/-2 expression and secretion were reduced (see FIG. 17, lower part), suggesting that meteorin regulates TSP-1/-2 expression via Erk1/2 pathway.

The present inventors also confirmed that TSP was located along with meteorin in the brain (P7) of the mouse on the 7$^{th}$ day of development (see FIG. 18), suggesting that meteorin plays a physiologically important role in TSP expression.

As explained above, meteorin regulates TSP-1/-2 expression, indicating its use as a TSP-1/-2 secretion promoter.

The present invention also provides a composition that comprises meteorin as an active ingredient for the prevention and treatment of angiogenesis related diseases including cerebrovascular disease, cardiovascular disease, ocular disease and cancer.

Angiogenesis related cerebrovascular disease includes multiple sclerosis (Rosenberg G. A., *Neuroscientist*, 8(6): 586-95, 2002), experimental allergic encephalomyelitis (Proescholdt M. A. et al., *J Neuropathol Exp Neurol.*, 61(10): 914-25, 2002), bacterial meningitis (Infect Dis Clin North Am., 13(3):527-48, v-vi. Review, 1999), ischemia (Gashe Y. et al., *J Cereb Blood Flow Metab.*, 21(12):1393-400, 2001), brain edema (Dempsey R J et al., *Neurosurgery.* 47(2):399-404; discussion 404-6, 2000), Alzheimer's disease (Banks W. A. et al., *Peptides,* 23(12):2223-6, 2002), acquired immune deficiency syndrome dementia complex (Krebs F. C. et al., *Adv Pharmacol.*, 49: 315-85, 2000), brain tumor (Davies D. C. et al., *J Anat.*, 200(6): 639-46, 2002), traumatic brain injury (Esen F. et al., *J Neurosurg Anesthesiol.*, 15(2): 119-25, 2003) and hypertension (Kucuk M. et al., *Life Sci.* 71(8): 937-46 2002).

Blood vessel maturation indicates that angiogenesis stops but the newly formed blood vessels gain functional maturity. Blood vessel maturation indicates that the blood-brain barrier is formed and thus selective permeability is induced. While the blood-brain barrier develops, angiogenesis in the brain stops and capillaries in the brain become differentiated into the blood-brain barrier (Plate, K. H., *J. Neuropathol. Exp. Neurol.*, 58, 313-320, 1999; Breier, G. et al., *Development* 114, 521-532, 1992).

Meteorin can be effectively used as a preventive and therapeutic agent for blood-brain barrier disorders since it can induce functional maturity of the blood-brain barrier by inhibiting angiogenesis.

Cardiovascular disease can be selected from the group consisting of arteriosclerosis, vascular synechia, and scleroedema (O'Brien K. D. et al., *Circulation* 93(4), pp 672-682, 1996). Ocular disease can be selected from the group consisting of keratoplastic angiogenesis, angiogenic glaucoma, macular degeneration, diabetic retinopathy, retinopathy of prematurity, angiogenic corneal disorder, pterygium, retinal degeneration, retrolental fibroplasia and trachoma (D'Amato R. J. et al., *Opthalmol.*, 102, pp 1261-1262, 1995, Adamis A. P. et al., *Angiogenesis*, 3, pp 9-14, 1999).

Cancer can be selected from the group consisting of astrocytoma, glioma, lung cancer, non-small cell lung carcinomas, hepatoma, colon carcinoma, bone cancer, pancreatic cancer, skin cancer, cervical cancer, melanoma, uterine cancer, ovarian cancer, rectal cancer, stomach cancer, anal cancer, colon carcinoma, breast cancer, fallopian tube carcinoma, endometrial carcinoma, cervical carcinoma, vaginal carcinoma, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penial cancer, prostatic cancer, bladder cancer, kidney or ureter cancer, renal cell carcinoma, pelvic carcinoma, central nervous system (CNS) tumor, primary CNS lymphoma, spinal cord tumor, and pituitary adenoma (Hanahan D et al., *Cell,* 86, pp 353-364, 1996). The invention can be applied for the treatment of angiogenesis associated cancer and metastasis.

The composition of the present invention can include, in addition to meteorin, one or more active ingredients having the same or similar functions to meteorin of the invention. The composition of the present invention can also include one or more pharmaceutically acceptable carriers for administration. The pharmaceutically acceptable carrier can be selected or be prepared by mixing more than one ingredient selected from the group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each disease or according to ingredients by following the method represented in Remington's Pharmaceutical Science (Mack Publishing Company, Easton Pa., 18th, 1990).

The composition of the present invention can be administered orally or parenterally (for example, intravenous, hypodermic, local or peritoneal injection). The effective dosage of the composition can be determined according to weight, age, gender, health condition, diet, administration frequency, administration method, excretion and severity of a disease. The dosage of the invention is 10~2,000 mg/kg per day, and preferably 50~500 mg/kg per day. The dosage of meteorin in the invention is 0.01~5000 mg/kg per day and preferably 0.01~10 mg/kg per day. Administration frequency is once a day or preferably a few times a day.

DESCRIPTION OF DRAWINGS

The application of the preferred embodiments of the present invention is best understood with reference to the accompanying drawings, wherein:

FIG. 1 is a photograph illustrating the purification of meteorin secreted from the cells transfected with meteorin gene:
 Mock: Mock vector; and
 α-c-myc: c-myc (oncogene) antibody.

FIG. 2 is a photograph illustrating the oxygen-dependent meteorin expression in human astrocytes:
 N: normoxia;
 H; hypoxia; and
 R; reoxygenation.

FIG. 3 is the set of a photograph and a graph illustrating the meteorin expression in each tissue of a mouse.

FIG. 4 is a photograph illustrating meteorin expression in the brains of the mouse in the embryonic stage and the mouse after birth FIG. 5 is a photograph illustrating meteorin immune response in the cerebral cortex of a mouse on the $7^{th}$ day after birth:
 Arrow: meteorin immune response.

FIG. 6 is a photograph illustrating meteorin immune response in the hippocampus of a mouse on the $7^{th}$ day after birth:
 Arrow: meteorin immune response;
 CA1: Ammon's horn 1;
 DG: dentate gyrus;
 H: Hilus;
 GCL: granular cell layer; and
 SGZ: subgranular zone.

FIG. 7 is a photograph illustrating the result of double immunofluorescence assay on meteorin in the endothelial cells of a mouse:
 PECAM: endothelial cell marker;
 DIC: equal distribution of meteorin and PECAM.

FIG. 8 is a photograph illustrating the result of double immunofluorescence assay on meteorin in pericytes of a mouse:
 αSMA: pericyte marker (alpha-SMA); and
 DIC: equal distribution of meteorin and -SMA.

FIG. 9 is a photograph illustrating the result of double immunofluorescence assay on meteorin in the astrocytes of a mouse:
 GFAP: astrocytes;
 DIC: equal distribution of meteorin and astrocytes.

FIG. 10 is a photograph illustrating meteorin immune response in the human embryo on the $39^{th}$ week:
 Arrow: meteorin immune response
 GCL: ganglion cell layer;
 IPL: innerplexiform layer; and
 INL: inner nuclear layer.

FIG. 11 is a photograph illustrating that the treatment of meteorin siRNA to human astrocytes results in the inhibition of endogenous meteorin expression:
 siN.C.: negative control not treated with meteorin siRNA;
 siMetr: astrocytes treated with meteorin siRNA;
 VEGF: vascular endothelial growth factor.

FIG. 12 is a photograph illustrating TSP-1/-2 expression after the treatment of meteorin to mouse astrocytes treated with meteorin siRNA:
 siMetr: medium obtained from astrocytes transfected with siRNA-meteorin (siMetr-ACM);
 VEGF: vascular endothelial growth factor.

FIG. 13 is a photograph illustrating tube-formation, endothelial cell migration and CAM (chorioallantoic membrane) expression after the treatment of human brain microvascular endothelial cells (HBMEC) with conditioned medium (siMetr-ACM) obtained from astrocytes transfected with meteorin siRNA:
 siN.C.: HBMEC non-treated with meteorin siRNA;
 siMetr: HBMEC treated with meteorin siRNA; and
 siMetr+TSP: HBMEC treated with meteorin siRNA and then 1 μg/ml of TSP protein (A and B) or 1 μg/ml of TSP protein (C) stepwise.

FIG. 14 is a photograph illustrating TSP-1/-2 expression after the treatment of different concentrations of meteorin to human astrocytes:
 Ang-1: giopoietin-1.

FIG. 15 is a graph illustrating the quantification of TSP-1/-2 expression of FIG. 14.

FIG. 16 is a photograph illustrating the tube-formation after exposing HBMEC on meteorin-treated astrocyte conditioned medium (Metr-ACM):
 con: HBMEC treated with vehicle alone;
 Metr: HBMEC treated with meteorin treated astrocyte conditioned medium;
 con+IgG: HBMEC treated with mouse IgG; and
 Metr-+α-TSP: HBMEC treated with Metr and neutralizing TSP-1/-2 antibody together.

FIG. 17 is a photograph illustrating the phosphorylated Erk1/2 in meteorin treated astrocytes:
 p-Erk1/2: phosphorylated Erk1/2.

FIG. 18 is a photograph illustrating the locations of meteorin and TSP-1/-2 in the brain of a mouse on the $7^{th}$ day after the birth.

MODE FOR INVENTION

Practical and presently preferred embodiments of the present invention are illustrative as shown in the following Examples.

The following examples illustrate the practical and preferred aspects of the present invention.

However, experts in the field, on consideration of this disclosure, may make modifications and improvements within the spirit and scope of the present invention.

Example 1

Preparation of Meteorin

To prepare meteorin, which is the active ingredient of the invention, CHO (Chinese hamster ovary) cells were transfected with the meteorin gene by using lipofectamin (Invitrogen, USA), followed by selection with geneticin (Gibco-BRL, USA). As a result, a stable meteorin cell line was prepared. The meteorin protein secreted in the above cell line was purified by column (Talon Metal affinity resin column, Clontech Laboratories Inc., USA) and the purified protein (FIG. 1) was concentrated by using Centricon YM10 (Millipore Corporation, USA) and dialyzed. The resultant product was used for the following experiments. Meteorin has the amino acid sequence represented by SEQ. ID. NO: 1 and the nucleotide sequence represented by SEQ. ID. NO: 2.

Example 2

Cell Culture

Human brain microvascular endothelial cells (HBMEC) and primary human cerebral cortex astrocytes used in the present invention were purchased from Cell Systems (USA). HBMEC was cultured in M199 medium supplemented with 20% FBS (fetal bovine serum, USA), 3 ng/ml of bFGF (Basic Fibroblast Growth Factor) and 10 units/ml of heparin and astrocytes were cultured in DMEM (Invitrogen, USA) supplemented with 10% FBS.

To establish hypoxic conditions in the following experiments, cells were cultured in a hypoxic chamber (Forma®) with 5% $CO_2$, $N_2$ and 1% $O_2$.

Conditioned media (CM) indicate the serum free DMEM loaded with astrocytes under each required experimental condition.

To eliminate endogenous meteorin, astrocytes were transfected with meteorin siRNA by using Astrocyte Nucleofactor™ kit (USA). To treat astrocytes with meteorin protein, the cells were cultured up to 50% of merging point and serum was not added before protein treatment. After culturing on CM without endogenous meteorin or with meteorin protein-treated astrocytes for 2~3 days, the cells were 50 fold concentrated by using Amicon® Ultra-4 centrifugal filter units (USA) for further experiments.

HBMEC was cultured in CM diluted with human endothelial serum-free basal medium (GibcoBRL, USA) at the ratio of 1:1.

Experimental Example 1

Oxygen-Dependent Meteorin Expression

To investigate how meteorin expression was affected by oxygen level in rat astrocytes, the present inventors produced affinity-purified anti-meteorin antibody designed to recognize meteorin. The meteorin-specific antibody was prepared by injecting a mouse meteorin-specific peptide $C^{28}SWRGSGLTQEPGSVGQ^{44}$ (amino acids 28 through 44 of SEQ. ID. NO: 14) to a rabbit as an antigen (Dinona Inc., USA and Takara, Korea).

Meteorin was slightly reduced under the hypoxic condition, compared with the normoxic condition. However, meteorin level was significantly increased under reoxygenation after hypoxia (FIG. 2). These results indicate that meteorin is a protein whose expression is regulated by oxygen level.

Experimental Example 2

Meteorin Expressions in Different Tissues

Meteorin expressions in different mouse tissues were examined by Northern blot analysis using meteorin cDNA as a probe (mouse multiple tissue northern; MTNTM, Clontech). As a result, meteorin expression in the brain was significantly high, compared with those in other tissues (FIG. 3).

Experimental Example 3

Regulation of Brain Development by Meteorin

As explained, meteorin is a protein largely expressed in the brain astrocytes and its expression is regulated by oxygen level. Therefore, the present inventors further investigated the brain development regulating function of meteorin. Western blotting was performed with the brains of the mouse in embryonic stage and the new born mouse. As a result, even though meteorin was detected both in the brain of new born and in the brain of an adult mouse, the expression of meteorin was slightly reduced as the brain continued to be developed (embryonic stage: on the $12.5^{th}$, $15.5^{th}$ and $17.5^{th}$ day; after birth: on the $3^{rd}$, $7^{th}$ and $20^{th}$ day) (FIG. 4).

Experimental Example 4

Meteorin Expression in Cerebral Cortex and Hippocampus

After confirming oxygen level dependent meteorin expression in astrocytes, the present inventors further investigated meteorin expression in the brain of a new born mouse. In particular, the present inventors investigated the stage in the brain of a new born mouse when angiogenesis and endothelial cell barrier formation are peculiar.

The brain of a ICR (IcrTacSam) mouse (Samtako, Korea) on the $7^{th}$ day after birth was extracted and frozen by sinking it in OCT compound (Sakura Finetek USA Inc., USA). Then, serial sections (10 µm) were prepared in the coronal direction. Immunohistochemical assay was performed with the sections using meteorin antibody. Perinuclear region was stained with hematoxylin as a counter staining and IgG was used as a control.

As a result, meteorin immune response was observed in almost every region of the cerebral cortex, and was particularly expressed in blood vessels with a star-shape structure (FIG. 5). Similar meteorin expression pattern was observed in the hippocampus, suggesting that meteorin immune response in star-shaped astrocytes is a kind of complex response closely associated with blood vessels (FIG. 6).

To distinguish cells that are able to express meteorin, double immunofluorescence assay was performed using antibiotics specific for meteorin immune response cells (meteorin), astrocytes (GFAP), pericytes (alpha-SMA, pericyte marker) and endothelial cells (PECAM, endothelial cell marker).

As a result, it was confirmed that the cells that responded to meteorin were astrocytes and that other endothelial cells or pericytes did not respond to meteorin (FIG. 7 and FIG. 8). In the image, dotted lines (DIC, differential interference contrast) indicate blood vessels.

An equal distribution of meteorin immune response and GFAP immune response was observed. This equal distribution is believed to be related to blood vessels and presented by DIC (dotted lines) (FIG. 9).

Experimental Example 5

Meteorin Expression in Retina

Retina and blood vessels therein developed from mesencephalon have selective barrier like characteristics, so that they are called the blood-retinal barrier (BRB). Retinal angiogenesis is similar to the formation of blood-brain barrier in morphological and developmental aspects. Thus, the present inventors investigated meteorin immune response in human retina under development. Eyes were isolated from a fetus of a patient at 39th week of pregnancy at Seoul National University Hospital, Seoul, Korea. Each eye was embedded in paraffin to prepare sections. Immunohistochemical assay was performed with those sections using InnoGenex immunohistochemistry kit (San Ramon, USA).

As a result, meteorin immune response was detected in GCL (ganglion cell layer), IPL (innerplexiform layer), and INL (inner nuclear layer) of a human fetus at the 39th week, when the selective barrier of blood vessels is formed (FIG. 10). As shown in the enlargement diagram, the meteorin expressing cells are shown in the region of the blood vessels of GCL and the blood vessels stretched from GCL to IPL and INL.

Experimental Example 6

Promotion of Angiogenesis of Human Brain Microvascular Endothelial Cells (HBMEC) by the Inhibition of Meteorin Expression in Astrocytes The present inventors performed tube formation analysis to investigate whether or not purified meteorin affected angiogenesis directly based on the founding that meteorin is largely expressed in astrocytes around blood vessels.

Meteorin purified in the above example was treated to human brain microvascular endothelial cells at different concentrations from 0.1 ng/ml to 1000 ng/ml. However, the purified meteorin did not affect the tube formation in HBMEC at any concentration.

The present inventors also investigated whether meteorin from human astrocytes affected blood vessels by inducing various signal factors involved in angiogenesis.

To confirm this hypothesis, an antibody able to recognize TSP-1 and TSP-2 simultaneously and an antibody specific for TSP-1 were used. TSP Ab-11 and -2 (LabVision Corporation, USA) were used as a TSP antibody for Western blotting. VEGF (vascular endothelial growth factor) antibody was purchased from Santa Cruz Biotechnology Inc (USA).

To inhibit endogenous meteorin expression in astrocytes, the present inventors designed siRNA encoding meteorin based on an internet program (such as provided by Dharmacon RNAi Technologies or the siRNA Selection Web Server provided by the Whitehead Institute for Biomedical Research) and prepared meteorin siRNA targeting human meteorin (5'-AACUGCAGGAGUCUGUCAUCA-3') (SEQ. ID. NO: 16) by adding dTdT to the sequence represented by SEQ. ID. NO: 13 (5'-CUGCAGGAGUCUGUCAUCA-3'). As a control, siRNA having a non-targeting sequence (non-targeting sequence as a negative control, siRNA NC) was prepared (Lafayette, USA).

Endogenous meteorin expression in astrocytes was inhibited by the above siRNA, the inhibition was confirmed by investigating cell lysate and conditioned medium. When endogenous meteorin was inhibited by siRNA, TSP-1/-2 expression and secretion in astrocytes were reduced but VEGF level was not changed (FIG. 11, left).

The inhibition of meteorin expression was also investigated at the level of mRNA. Total RNA was extracted from the mouse brain or human astrocytes according to the manufacturer's instruction using trizol (Invitrogen, USA). From the total RNA, first-stranded cDNA was synthesized by using a reverse transcriptase (murine leukemia virus reverse transcriptase, USA) and then an equal amount of cDNA was amplified by PCR with a pair of mouse meteorin primers (SEQ. ID. NO: 3; 5'-TCCGCTCACGCTGGCTACTCG-3' and SEQ. ID. NO: 4; 5'-GCAGCTCTGTGTCATGGGCGAC-3'), a pair of human meteorin primers (SEQ. ID. NO: 5; 5'-ATGGGGTTCCCGGCCG-3' and SEQ. ID. NO: 6; 5'-GTGCAGCGCCACCTCGC-3'), a pair of human TSP-1/-2 primers (SEQ. ID. NO: 7; 5'-CTGGACAGCTCATCACAGGA-3' and SEQ. ID. NO: 8; 5'-TTGTCTTTGGAACCACACCA-3') and a pair of β-actin primers (SEQ. ID. NO: 9; 5'-GACTACCTCATGAAGATC-3' and SEQ. ID. NO: 10; 5'-GATCCACATCTGCTGGAA-3').

As a result, TSP-1/-2 mRNA was reduced (FIG. 11, right).

To verify that the above decrease of TSP-1/-2 mRNA was not because of siRNA itself, the present inventors applied purified meteorin to the astrocytes treated with meteorin siRNA and obtained the conditioned medium 72 hours later. The application of purified meteorin at 0.1 ng/ml and 1 ng/ml (FIG. 12) resulted in the recovery of TSP-1/-2 expression to the original level. This result indicates that the decrease of mRNA was not due to the siRNA itself.

TSP-1/-2 expression and secretion were reduced when the endogenous meteorin expression was inhibited in astrocytes. Thus, the indirect effect of meteorin on HBMEC was further investigated by using the conditioned medium (siMetr-ACM) obtained from the astrocytes transfected with siRNA-meteorin.

The present inventors confirmed the tube formation with 'BD Matrigel™ assay' (BD Bioscience, USA). Particularly, 5×10[4] HBMECs were seeded in a 48 well plate (Nunc, Denmark), to which the conditioned medium (siMetr-ACM) obtained from astrocytes was added. 4 hours later, changes in cell morphology were observed. TSP protein and heparin used for the investigation of tube formation were purchased from Sigma-Aldrich Corporation (USA) and bFGF (basic fibroblast growth factor) was purchased from Upstate Biotechnology (USA). Wound migration assay was performed to examine the microvascular endothelial cell migration and CAM assay was performed to investigate the CAM (chorioallantoic membrane) expression.

Wound migration assay was performed as follows.

1.5×10[6] HBMECs were inoculated to a 60 mm dish coated with 0.3% gelatin, followed by culture at 37° C. for 1~2 days until 90% confluency was obtained. Wounding was executed with a sterilized plastic tip. After washing three times with PBS (phosphate buffered saline) to completely eliminate cell debris, the conditioned medium and 1 mM of thymidine were added, followed by further culture at 37° C. for 16 hours. After two more washes with PBS, the cells were fixed with methanol for one minute and stained with Giemsa solution for 5 minutes and then the number of migrated cells was measured under a microscope.

CAM analysis was performed as follows.

A fertilized egg was cultured in a 37° C. incubator with 90% humidity. On the 3rd day of culture, a hole was made by a knife through which 3 ml of albumin was drawn out with a syringe. On the 9th day of culture, a sterilized cover slip (Nnnc, Rochester, USA) layered with the conditioned medium was placed while avoiding large blood vessels. After culturing for 2 days in the incubator, 2~3 ml of 10% fat emulsion (Intralipose) were added to the inside of CAM, followed by observation under the dissecting microscope (×8) and photographs of CAM.

As a result, siMetr-ACM increased the tube formation, the microvascular endothelial cell migration and CAM (choioallantoic membrane) expression. The effect of siMetr-ACM on angiogenesis was inhibited by TSP treatment (FIG. 13).

Experimental Example 7

Angiogenesis Inhibitory Effect of Meteorin by Regulating TSP-1/-2 Expression and Secretion in Astrocytes

To investigate the mechanism of TSP expression induced by meteorin, the present inventors examined TSP-1/-2 expression by Western blot analysis after applying meteorin to human astrocytes at different concentrations.

Human astrocytes were cultured for 16 hours in serum-free medium and then treated with meteorin for 40 hours at different concentrations (0, 0.1, 0.3, 1, 3 and 10 ng/ml). AB-11 (Lab Vision Corporation, CA) was used as a TSP antibody. The result of Western blotting confirmed that meteorin induced TSP-1/-2 expression in cell lysate and conditioned medium.

TSP-1/-2 expression increased meteorin dose-dependently in conditioned medium. However, giopoietin-1 level was not changed (FIG. 14). FIG. 15 illustrates the quantification of TSP-1/-2, measured by densitometry.

The present inventors examined the effect of meteorin on the tube formation using the conditioned medium. The conditioned medium obtained from astrocytes treated with meteorin was added to HBMEC, followed by culture for 4 hours. When the HBMEC was exposed to the conditioned medium (Metr-ACM) obtained from astrocytes treated with meteorin at 0.3 ng/ml, tube formation was inhibited (FIG. 16). To verify that the angiogenesis inhibitory effect was attributed to TSP-1/-2, the present inventors performed the following experiment using a TSP neutralizing antibody (Ab-1, Lab Vision Corporation, CA).

The application of the neutralizing antibody resulted in the nullification of angiogenesis inhibitory effect (FIG. 16, Metr-+α-TSP), suggesting that the TSP-1/-2 in Metr-ACM mediates the angiogenesis inhibitory activity. In FIG. 16, "con" indicates vehicle-treatment only and "con+IgG" indicates co-treatment with mouse IgG.

According to a recent report, the activation of ERK1/2 and Akt 1 pathway contributes to the expression of TSP-1/-2. So, the present inventors treated astrocytes with 10 ng/ml of meteorin for 10 minutes and performed Western blotting using Erk1/2 and phosphor Erk1/2 antibodies (Cell Signaling Technology Inc., USA). As a result, Erk1/2 phosphorylation was induced when meteorin protein was applied to astrocytes (FIG. 17, upper part).

Astrocytes were treated with 1 uM of U0126 (Cell Signaling Technology Inc., USA), a MEK [Mitogen-Activated Protein (MAP) Kinase] inhibitor, followed by 10 ng/ml of meteorin. The cells were cultured for 24 hours and Western blotting was performed. As a result, TSP-1/-2 expression and secretion were reduced in the astrocytes treated with U0126 (FIG. 17, lower part), indicating that meteorin regulates TSP-1/-2 expression via Erk1/2 signal pathway.

The present inventors located meteorin and TSP-1/-2 in the developing brain. Immune response was induced by using TSP specific antibody Ab-4 (Lab Vision Corporation, CA). As a result, the inventors confirmed that TSP is located together with meteorin in the brain (P7) of a mouse on the $7^{th}$ day of development (FIG. 18). In FIG. 18, meteorin is colored as green and TSP is colored as red and the location where these two proteins exist together is colored as yellow.

INDUSTRIAL APPLICABILITY

As previously explained, Meteorin is expressed in primary cultured human astrocytes and mouse GFAP positive astrocytes with spurs that surround blood vessels in the brain and retina and with endfeet that envelop endothelial cells of mice after their birth. The meteorin is expressed with TSP-1/-2, inhibits angiogenesis and plays an important role in blood vessel maturation. Therefore, the meteorin of the present invention can be effectively used for the development of a pharmaceutical composition for the prevention of vascular disease, as an angiogenesis inhibitor, as a thrombospondin-1/-2 (TSP-/-2) secretion stimulator, and for health foods that prevent vascular disease.

[Sequence List Text]

SEQ. ID. NO: 1 is the polypeptide sequence of a rat meteorin.

SEQ. ID. NO: 2 is the polynucleotide sequence of a rat meteorin.

SEQ. ID. NO: 3 is the sense primer sequence for the amplification of a mouse meteorin gene.

SEQ. ID. NO: 4 is the antisense primer sequence for the amplification of a mouse meteorin gene.

SEQ. ID. NO: 5 is the sense primer sequence for the amplification of a human meteorin gene.

SEQ. ID. NO: 6 is the antisense primer sequence for the amplification of a human meteorin gene.

SEQ. ID. NO: 7 is the sense primer sequence for the amplification of a human TSP-1/-2 gene.

SEQ. ID. NO: 8 is the antisense primer sequence for the amplification of a human TSP-1/-2 gene.

SEQ. ID. NO: 9 is the sense primer sequence for the amplification of a β-actin gene.

SEQ. ID. NO: 10 is the antisense primer sequence for the amplification of a β-actin gene.

SEQ. ID. NO: 11 is the polypeptide sequence of a human meteorin.

SEQ. ID. NO: 12 is the polynucleotide sequence of a human meteorin.

SEQ. ID. NO: 13 is the polynucleotide sequence of a meteorin siRNA.

SEQ. ID. NO: 14 is the polypeptide sequence of a mouse meteorin.

SEQ. ID. NO: 15 is the polynucleotide sequence of a mouse meteorin.

Experts in the field will appreciate that the conceptions and specific embodiments disclosed in the aforementioned description may be readily utilized as a basis for modifying or designing other embodiments for carrying out the same purposes of the present invention. Experts in the field will also appreciate that such equivalent embodiments do not depart from the spirit and scope of the invention as set forth in the appended claims.

The invention claimed is:

1. A method of inhibiting angiogenesis in cells, a cell line, or a tissue comprising astrocytes, said method comprising administrating a meteorin to said cells, cell line or tissue in an effective amount for inhibiting angiogenesis in the cells, a cell line, or a tissue, wherein the meteorin is a protein comprising the amino acid sequence of SEQ. ID. No: 11 or No:14.

2. The method as set forth in claim 1, wherein the meteorin enhances the secretion of thrombospondin-1/-2 (TSP-1/-2).

3. The method of claim 1, wherein the meteorin is a protein comprising the amino acid sequence of SEQ. ID. NO: 11.

4. The method of claim 1, wherein the meteorin is a protein comprising the amino acid sequence of SEQ. ID. NO: 14.

5. The method of claim 1, wherein the protein is encoded by DNA comprising the coding region of the nucleotide sequence of SEQ. ID. No:2, No: 12 or No: 15.

* * * * *